United States Patent
Wuite et al.

(10) Patent No.: US 9,766,180 B2
(45) Date of Patent: Sep. 19, 2017

(54) METHOD AND SYSTEM FOR IMAGING A MOLECULAR STRAND

(71) Applicant: Stichting VU-VUmc, Amsterdam (NL)

(72) Inventors: Gijs Jan Lodewijk Wuite, Amsterdam (NL); Erwin Johannes Gerard Peterman, Amsterdam (NL); Iddo Heller, Amsterdam (NL); Gerrit Sitters, Amsterdam (NL); Andrea Candelli, Amsterdam (NL); Stefan Walter Hell, Amsterdam (NL)

(73) Assignee: Stichting VU-VUmc, Amsterdam (NL)

( * ) Notice: Subject to any disclaimer, the term of this patent is extended or adjusted under 35 U.S.C. 154(b) by 0 days.

(21) Appl. No.: 14/895,477

(22) PCT Filed: Jun. 2, 2014

(86) PCT No.: PCT/NL2014/050351
§ 371 (c)(1),
(2) Date: Dec. 2, 2015

(87) PCT Pub. No.: WO2014/196854
PCT Pub. Date: Dec. 11, 2014

(65) Prior Publication Data
US 2016/0139050 A1    May 19, 2016

(30) Foreign Application Priority Data

Jun. 3, 2013   (EP) .................................. 13170323
Jul. 3, 2013   (NL) .................................. 2011087

(51) Int. Cl.
*G01N 33/00*    (2006.01)
*G01N 35/00*    (2006.01)
(Continued)

(52) U.S. Cl.
CPC .... *G01N 21/6428* (2013.01); *B01L 3/502761* (2013.01); *G01N 21/6458* (2013.01);
(Continued)

(58) Field of Classification Search
CPC ........ G01N 33/00; G01N 35/00; G01N 21/00; G01N 21/75; G01N 21/64; G01N 21/66; C12Q 1/68
(Continued)

(56) References Cited

U.S. PATENT DOCUMENTS 5,512,745 A   4/1996   Finer et al.
5,731,588 A   3/1998   Hell et al.
(Continued)

FOREIGN PATENT DOCUMENTS

WO   WO 2007/038260 A2   4/2007

OTHER PUBLICATIONS

Brau et al., "Interlaced Optical Force-Fluorescence Measurements for Single Molecule Biophysics," *Biophysical Journal*, vol. 91, Aug. 2006, pp. 1069-1077.
(Continued)

*Primary Examiner* — Brian J Sines
(74) *Attorney, Agent, or Firm* — Kilpatrick Townsend & Stockton LLP

(57) ABSTRACT

The present disclosure concerns a method and system for imaging a molecular strand (MS). The method comprises providing a sample volume (SV) comprising the strand (MS); providing an excitation beam (EB) having an excitation focus (EF) in the sample volume (SV); scanning the excitation focus (EF) in the sample volume (SV) along a one dimensional scanning line (SL); trapping an end of the strand (MS) in the sample volume (SV) and extending the strand (MS) along a one-dimensional trapping line (LL) parallel to the scanning line (SL); aligning the trapping line
(Continued)

(LL) to coincide with the scanning line (SL) to have the scanning excitation focus (EF) coincide with the strand (MS); and recording the fluorescence response (FR) as a function of a plurality of distinct scanning positions (X0) of the excitation focus (EF) along the scanning line (SL).

13 Claims, 22 Drawing Sheets

(51) Int. Cl.
    *G01N 21/00*     (2006.01)
    *C12Q 1/68*     (2006.01)
    *G01N 21/64*     (2006.01)
    *B01L 3/00*     (2006.01)
    *G02B 21/00*     (2006.01)
    *G02B 21/16*     (2006.01)
    *G02B 21/32*     (2006.01)

(52) U.S. Cl.
    CPC ..... *G02B 21/0048* (2013.01); *G02B 21/0076* (2013.01); *G02B 21/16* (2013.01); *G02B 21/32* (2013.01); *B01L 2200/0663* (2013.01); *B01L 2300/0877* (2013.01); *B01L 2400/0454* (2013.01); *C12Q 1/6816* (2013.01)

(58) Field of Classification Search
    USPC ........... 422/68.1, 82.05, 82.07, 82.08; 435/4, 435/6.1, 6.11; 436/131, 164, 172, 800, 436/43, 94
    See application file for complete search history.

(56) References Cited

U.S. PATENT DOCUMENTS

| | | | |
|---|---|---|---|
| 9,176,311 B2 * | 11/2015 | Yamamoto | |
| 2004/0033515 A1 * | 2/2004 | Cao et al. | 435/6 |
| 2004/0207854 A1 | 10/2004 | Hell et al. | |
| 2005/0023156 A1 * | 2/2005 | Ramsey et al. | 205/792 |
| 2009/0023146 A1 * | 1/2009 | Harnack et al. | 435/6 |
| 2009/0111115 A1 * | 4/2009 | Drmanac et al. | 435/6 |
| 2010/0029508 A1 * | 2/2010 | Austin et al. | 506/16 |
| 2010/0176307 A1 | 7/2010 | Hell et al. | |
| 2010/0251437 A1 | 9/2010 | Heyn et al. | |
| 2011/0201509 A1 | 8/2011 | Tegenfeldt et al. | |
| 2011/0226623 A1 * | 9/2011 | Timp et al. | 204/543 |
| 2011/0300490 A1 | 12/2011 | Rachet et al. | |
| 2011/0308949 A1 * | 12/2011 | Afzali-Azdakani et al. | 204/451 |
| 2012/0002031 A1 | 1/2012 | Pertsinidis et al. | |
| 2014/0194314 A1 * | 7/2014 | Walsworth et al. | 506/9 |
| 2014/0238856 A1 * | 8/2014 | Ramsey et al. | 204/452 |

OTHER PUBLICATIONS

Candelli et al., "Combining optical trapping, fluorescence microscopy and micro-fluidics for single molecule studies of DNA-protein interactions," 2011, *Phys. Chem. Chem. Phys.* 13: 7263-7272.

Comstock et al., "Ultrahigh-resolution optical trap with single-fluorophore sensitivity," *Nature Methods*, vol. 8, No. 4, Apr. 2011, pp. 335-343.

Forget et al., "Exploring protein-DNA interactions in 3D using in situ construction, manipulation and visualization of individual DNA dumbbells with optical traps, microfluidics and fluorescence microscopy," 2013, *Nature Protocols*, vol. 8, No. 3, pp. 525-538.

Laurens et al., "Alba shapes the archaeal genome using a delicate balance of bridging and stiffening the DNA," 2012, *Nature Communications*, 3:1328 doi: 10.1038/ ncomms2330.

Donnert, et al., "Macromolecular-scale resolution in biological fluorescence microscopy," *Proc. Natl Acad. Sci. USA*, vol. 103, No. 31, pp. 11440-11445 (2006).

Hell, et al., "Breaking the diffraction resolution limit by stimulated emission: stimulated-emission-depletion fluorescence microscopy," *Opt. Lett.*, vol. 19, No. 11, pp. 780-782 (1994).

Moneron, et al., "Fast STED microscopy with continuous wave fiber lasers," *Opt. Express.*, vol. 18, No. 2, pp. 1302-1309 (2010).

International Search Report for International Application No. PCT/NL2014/050351 dated Jul. 17, 2014.

* cited by examiner

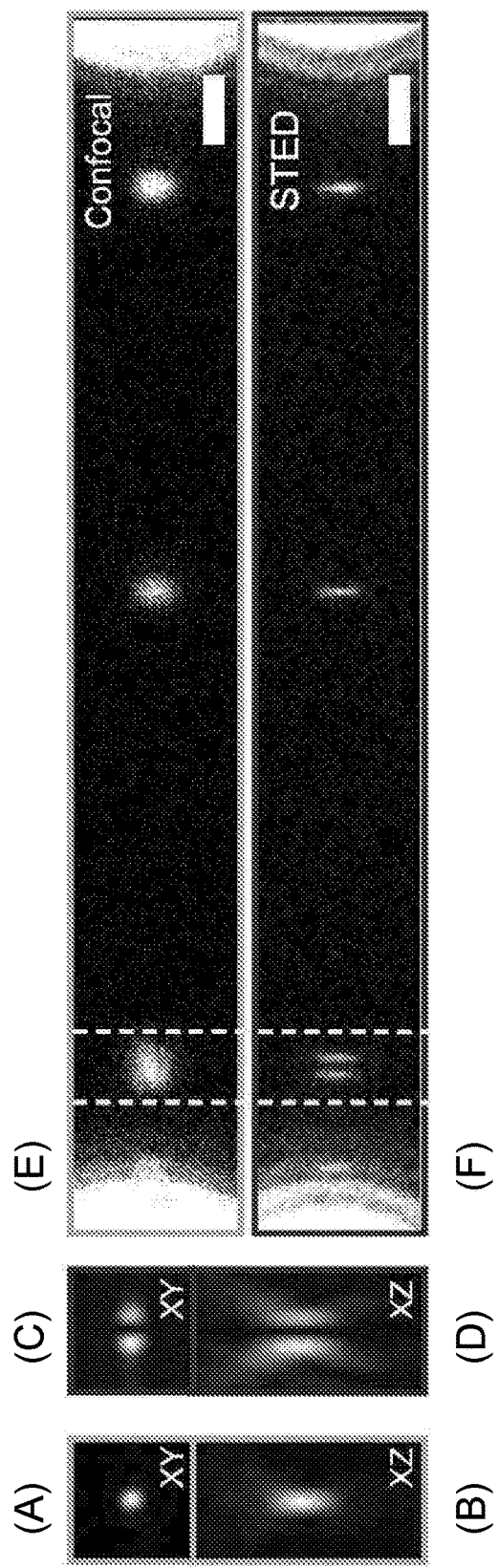
FIG. 10A-F

METHOD AND SYSTEM FOR IMAGING A MOLECULAR STRAND

TECHNICAL FIELD AND BACKGROUND

The present disclosure concerns a method and system for imaging a molecular strand, e.g. a molecular complex such as DNA.

The interaction between nucleic acids (e.g. DNA and RNA) and proteins plays an important role in the molecular biology of the cell, being at the heart of DNA replication, transcription, organization, and repair. Not only is understanding these processes important to understanding life in itself; it is also desired for generating key insights into disease mechanisms. Fluorescence microscopy and force spectroscopy using optical tweezers are two pillars of single-molecule research.

Optical tweezers are used for measurement of global mechanical and structural properties of DNA-protein complexes. These measurements can be related to coinciding fluorescent emissions. For example, Lang et al. (Nat. Methods 1, 2004, 133-139) describe simultaneous, coincident optical trapping and single-molecule fluorescence wherein mechanical transitions in the structure of DNA are probed by analyzing fluctuations in fluorescence intensity within a fixed confocal volume.

Fluorescence microscopy can provide local structural information. For example, Candelli et al. (Phys. Chem. Chem. Phys., 2011, 13, 7263-7272) describe a method integrating optical trapping with micro-fluidics and single-molecule fluorescence microscopy to study heterogeneous/complex protein interactions. This combination of wide-field fluorescence microscopy and optical tweezers allows localization of labelled proteins on optically stretched DNA with sub-10 nm (nanometer) precision at tensions above 1 pN (pico-Newton).

US 2011/0201509 by Tegenfeldt discloses a method for the mapping of the local AT/GC ratio along the DNA in which the DNA is denaturated to partially melt a double-stranded DNA molecule depending e.g. on temperature. The method includes staining DNA with a fluorescent dye, the emission of which is sensitive to whether the DNA is single stranded or double stranded. The DNA is introduced with a flow into a nanochannel device that if necessary stretches the DNA to prevent overlap of different segments of the molecule. The basic tool for observing the resulting pattern of the DNA is diffraction limited standard fluorescence microscopy. Once raw movies of denatured molecules are acquired, a software program is used to align the barcode fluorescence pattern across the images as a function of time.

US 2012/0002031 by Pertsinidis discloses a microscope that provides sub-nanometer resolution in measurements of molecular-scale distances using far-field fluorescence imaging optics. This performance is achieved using feedback control of the position of individual fluorescent molecules, allowing collection of >$10^6$ photons locked at the same position. The imaging system is calibrated by raster scanning a fluorescent emitter and correcting imperfections at pixel and subpixel scales by comparing the position of the fluorescence image and the known displacement of the sample, using a sub-nm accurate piezo translation stage. A sample arrangement is illustrated in which an end of a DNA molecule is attached to a surface and the other end is held in an optical trap.

There is yet a desire for a method and system providing improved control and accuracy for the imaging of a molecular strand.

SUMMARY

A first aspect of the present disclosure provides a method for imaging a molecular strand, the method comprising providing a sample volume comprising the strand; providing an excitation beam having an excitation focus in the sample volume wherein an excitation of a fluorophore on the strand by the excitation focus results in a fluorescence response when the excitation focus coincides (e.g. overlaps) with the fluorophore; scanning the excitation focus in the sample volume along a one dimensional scanning line; trapping an end of the strand in the sample volume and extending the strand along a one-dimensional trapping line parallel to the scanning line; aligning the trapping line to coincide with the scanning line to have the scanning excitation focus coincide with the strand; and recording the fluorescence response as a function of a plurality of distinct scanning positions of the excitation focus along the scanning line.

By extending the molecular strand along a straight (one-dimensional) trapping line, scanning a probe beam along a scanning line parallel to the trapping line, and aligning the trapping line and scanning line to coincide, the molecular strand can be accurately imaged in a controlled and reproducible manner. It is recognized that the one-dimensional trapping and scanning is specifically tailored for imaging a molecular strand which can be considered a one-dimensional object for imaging purposes. Because only the dimension of the molecular strand is scanned, the scanning can be better controlled, the imaging more accurate, and faster. In contrast, the prior art of e.g. US 2011/0201509 and US 2012/0002031 essentially relies on two-dimensional fluorescence imaging and not a one-dimensional scanning line. The mention of STED microscopy does not imply one-dimensional scanning along a trapping line or otherwise. In particular, it is noted that STED is conventionally used for producing two-dimensional images as described for example in the articles by Donnert et al. (PNAS, part 103, nr. 31, p. 11440) and Gael Moneran et al. (Optics Express, part 18, nr. 2, p. 1302).

The use of a one dimensional scanning line provides also additional advantages. For example, by repeatedly scanning the excitation focus back and forth along the scanning line, the fluorescence response can be recorded as a function of the signal can be integrated over multiple scans to increase the signal. Alternatively or in addition, the signal can also be recorded as a function of time to track changes of the molecular strand or molecular complex.

By providing a second beam which decreases the spatial spread of the excited fluorophores by stimulated emission depletion (STED) of the fluorophore, resolution of the imaging can be improved beyond the diffraction limit, e.g. also depending on power in STED beam (see below). However, the smaller effective focus size can provide additional difficulties in beam alignment. By providing the depletion profile with a stripe or plane of minimum intensity extending in a direction perpendicular to the trapping line, as opposed to a round donut shaped depletion profile, sensitivity to misalignment of the beam can be decreased, in particular for the presently disclosed one-dimensional scanning of the strand. By having a STED profile shaped as a line or plane perpendicular to the direction of the extended strand, fluctuations in the positioning of the beam and/or strand in the said perpendicular direction may have a less or negligible influence on the fluorescence signal.

By using optical traps to hold the molecular strand, alignment control can be improved. The optical traps can be aligned to have the trapping line between trapped beads coincide with the scanning line. Advantageously, optical traps holding opposite ends of the strand can be used to freely manipulate the angle and position of the trapping line in three dimensional space. In particular, the optical traps with the strand therein between can be positioned to be parallel and fully coincide with a one-dimensional scanning line.

It is noted that neither the nanochannels of US 2011/0201509 nor the single optical trap of US 2012/0002031 allow free manipulation of the strand in three dimensional space. While US 2011/0201509 mentions optical tweezers, it is not detailed how many or why this should be implemented. For example, the force and/or heat generated by optical tweezers can influence the denaturing on which this prior art relies (this would also apply to a scanning focal spot).

One method for the alignment (in Z) comprises recording a series of two dimensional images of the stained strand for different axial positions of the optical traps with respect to the scanning line. The inventors find that by minimizing a line thickness of the strand (XY) in the images and/or by maximizing a contrast of the strand in the images while varying a position of the object plane with respect to the trapping line (in Z), an optimal overlap between the trapping line and scanning line can be found. Advantageously, the optical traps can furthermore allow adjusting and measuring of the tensile force exerted on the strand. The inventors find that by exerting a tensile force on the strand large enough to suppress the Brownian fluctuations below the imaging resolution (in the case of Lambda DNA, of length of 16.4 of more than 5 pN, preferably more than 10 pN, the imaging resolution (Full-width half maximum of the recorded signal FWHM) can be improved, in particular the resolution can be optimized in conjunction with the STED beam improvement.

Without wishing to be bound by theory, the inventors recognize that the ultimate resolution may depend on the optical resolution (STED power, wavelength of light used, type of objective lens pinhole size etc.); on the stiffness of the strand (the length of the strand, molecular structure etc.); on the position of imaged features along the strand; and on the tension (temperature, stiffness of traps etc.). For example, thermal fluctuation of the strand blurs images of features on the strand. This blurring deteriorates the effective resolution of images to a value that is worse than the optical resolution. The effective resolution can be enhanced by applying tension to the strand to suppress its thermal fluctuations. In particular, to improve the effective resolution of images of the strand to a value better than the diffraction-limit (e.g. by the STED technique) the inventors find that a tensile force needs to be exerted. It is noted that effective FWHM (=resolution) decreases with tension. The resolution is only diffraction limited at high tension. For example, localization precision may enhance with tension to about 10 nm precision. The localization precision can be better than the diffraction limit. It is noted that there is an important difference between "resolution" and "localization precision": resolution refers directly to the closest distance between two imaged objects for which one can still distinguish those two objects. Localization precision, on the other hand, relates to the precision with which one can localize the position of one object by averaging multiple measurements of its location with a certain resolution. This averaging allows to localize with a precision that is higher than the resolution. The crucial difference is that localization only works for isolated objects. If a second object is present at a distance closer than the resolution, and the two objects are imaged at the same time, than one can no longer distinguish the two objects, and thus cannot localize them. The present technique allows to distinguish two objects that are closer than the diffraction limit, under the condition that one can apply a tension large enough to suppress the thermal fluctuations of the strand. It will appreciated that this is quite different from known techniques, e.g. as described in the aforementioned article by Candelli et al., and provides a key to the ability to go to higher densities of objects on DNA.

It is presently recognized that localization accuracy of fluorophores and/or temporal resolution can be enhanced by lateral 1D-scanning using a STED shape (stripe or donut-STED shape). Without wishing to be bound by theory, the inventors find that localization precision $\Delta X$ of a feature (e.g. fluorescent protein on a strand of DNA) due to photon-counting noise scales as $\Delta X \propto FWHM/\sqrt{N_{photons}}$, wherein FWHM is the imaging resolution (Full Width Half Maximum of recorded features) and $N_{photons}$ is the number of photons recorded from the feature. If a fluorophore is imaged by 1D scanned STED, $N_{photons}$ scales as FWHM, assuming the same peak amplitude. When this scaling is included into the above formula, we obtain $\Delta X \propto FWHM/\sqrt{FWHM} = \sqrt{FWHM}$. Consequently the inventors find that by decreasing the FWHM, localization precision can be enhanced, or temporal resolution enhanced for a given localization precision because less photons are needed to obtain the same precision. In contrast, when using 2D scanning with a STED donut and 2D localization, $N_{photons}$ scales as $FWHM^2$, therefore, $\Delta X \propto FWHM/\sqrt{FWHM^2} \propto 1$, i.e. independent of FWHM, and there is no improvement expected in the localization accuracy of fluorophores and/or temporal resolution.

By using a confocal setup, background light originating away from the focal plane (object plane) can be filtered. By trapping and extending the entire strand in the focal plane, the strand can be imaged without moving the focal plane with improved background rejection, e.g. labelled proteins (fluorophores) in the background. Advantageously, the strand does not have to be moved to another location where no proteins in solution are present, or these proteins need not be flushed away. This enables measurements of the strand in higher concentrations of labelled proteins, e.g. a factor 100 times higher than with wide field imaging, better mimicking in vivo conditions.

A second aspect of the present disclosure provides a system for imaging a molecular strand, the system comprising a sample cell arranged for providing a sample volume comprising the strand; an excitation light source arranged for providing an excitation beam having an excitation focus in the sample volume wherein an excitation of a fluorophore on the strand by the excitation focus results in a fluorescence response when the excitation focus coincides with the fluorophore; a beam scanner arranged for scanning the excitation focus in the sample volume along a one dimensional scanning line; a trap arranged for trapping an end of the strand in the sample volume and extending the strand along a one-dimensional trapping line parallel to the scanning line; a beam aligner arranged for aligning the trapping line to coincide (e.g. overlap) with the scanning line to have the scanning excitation focus coincide with the strand; and a fluorescence detector arranged for recording the fluorescence response as a function of a plurality of distinct scanning positions of the excitation focus along the scanning line; and a processor programmed to provide a scanning mode wherein the processor controls the trap to extend the strand along a one-dimensional trapping line in the first direction; the processor controls the beam aligner to have the trapping line coincide with the scanning line; the processor controls the beam scanner to scan the excitation focus along the scanning line; the processor receives the recorded fluorescence response from the fluorescence detector; and the processor stores the fluorescence response as a function of a position of the excitation focus along the scanning line.

The system is arranged for performing the method according to the first aspect to provide similar advantages.

BRIEF DESCRIPTION OF DRAWINGS

These and other features, aspects, and advantages of the apparatus, systems and methods of the present disclosure will become better understood from the following description, appended claims, and accompanying drawing wherein:

FIG. 10A-I illustrates characterization of STED nanoscopy of proteins on optically stretched DNA;

DESCRIPTION OF EMBODIMENTS

Figure 1A:
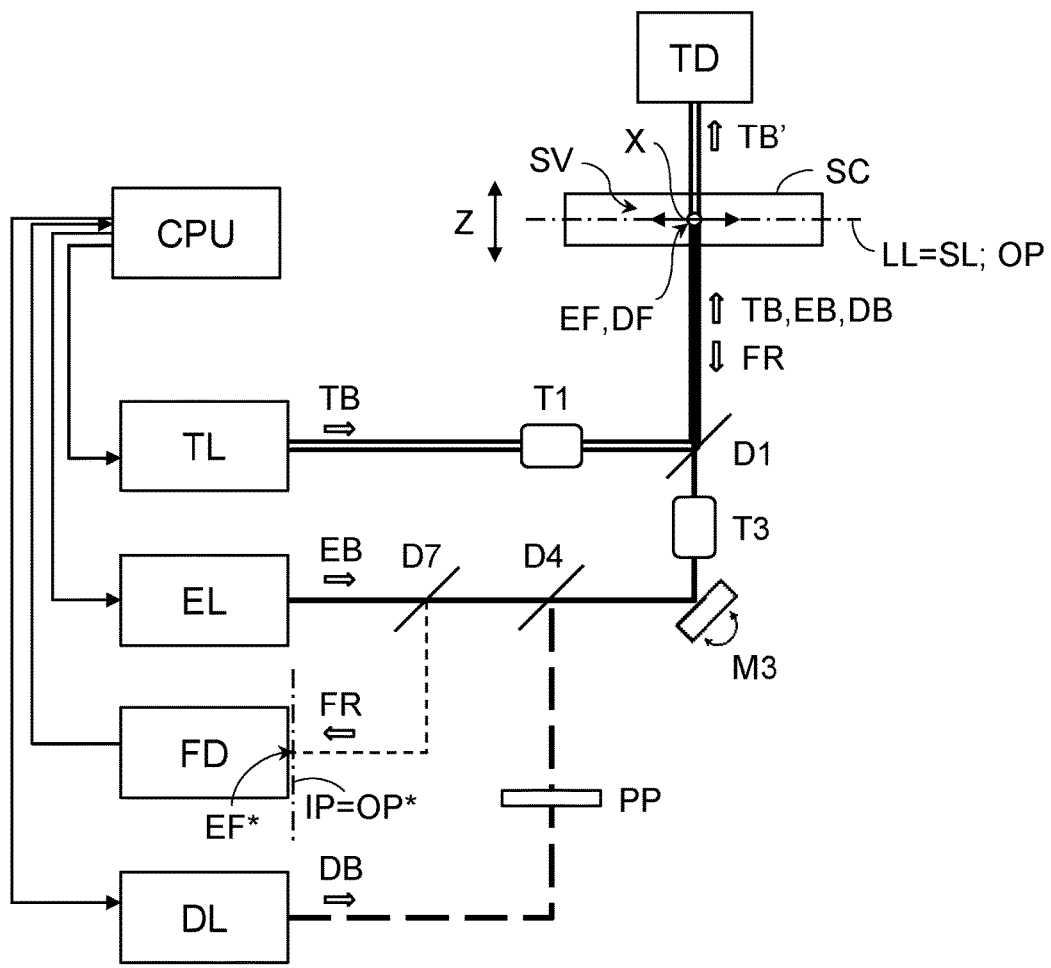
FIG. 1A illustrates an embodiment of a system and method for imaging a molecular strand.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

It is noted that for consistency, a three dimensional Cartesian coordinate system with X, Y, Z coordinates will be used throughout the description. The X-axis is defined as the axis parallel to the molecular strand or trapping line. The term "strand" as in "molecular strand" refers to an essentially one-dimensional structure or complex such as a strand of DNA that can be arranged along the X-axis. Of course the application of the disclosure is not restricted to DNA, but applications can also be envisioned to other linear molecules or molecular assemblies, including, but not limited to, proteins, polysaccharides, organic polymers, carbon nanotubes and fibrous inorganic materials. When imaging the molecular strand, also molecules attaching to the strand (e.g. proteins) can be imaged. The XY plane is the object plane to be imaged and is generally transverse to the incoming beams and imaged on the detector. The Z axis is perpendicular to the object plane. The XYZ coordinate system is used for illustration purposes only to better explain the relative positioning and orientation. Of course also other reference frames and coordinate systems can be used without departing from the present scope.

One aspect of the present disclosure provides a method and instrument that permit the study of nucleic acid-protein interactions in real-time under real-life conditions (DNA densely covered with proteins and high proteins concentration present in solution). It enables direct visualization of DNA-protein interactions in real-time, at the single-molecule level, at sub-diffraction resolution, under conditions similar to the cellular environment. Using this method, researchers can manipulate and measure mechanical and structural properties of DNA-protein complexes, while simultaneously performing super resolution visualization, which allows distinguishing entities at separations below the diffraction limit and localizing these entities with enhanced spatiotemporal resolution.

Advantages provided by practice of the present teachings may include:

The capability of visualizing and localizing individual fluorescently labelled proteins bound on a single DNA molecule held suspended in solution. Individual proteins on DNA can be resolved with a resolution below 50 nm: an improvement of at least 6-fold over conventional fluorescence microscopy under the same conditions The possibility of performing experiments in conditions mimicking the real cellular situation, such as dense protein coverage of DNA and high protein concentrations in solution, without loss of signal or resolution;

Single DNA molecules can be manipulated with high precision (sub-pico-Newton force resolution), while its extension can be controlled with nanometer accuracy;

Use of fast line scanning along DNA allows high-speed imaging, permitting the observation of protein dynamics on DNA at high time resolution (e.g. less than 50 ms).

This methodology does not only enhance the quality of obtained data, it also makes a new class of experiments of biological relevance possible. It allows bridging the gap between idealized single-molecule experiments (low concentration of proteins in solutions and few proteins bound on the DNA) and realistic in vivo experiments, e.g. high density of proteins on DNA in solution. The combination of different research technologies into an integrated platform, can provide the future of quantitative biological research, focused on unravelling the complete and detailed mechanisms of DNA-protein interactions. In one aspect, the presently disclosed methods marries the super-resolution microscopy field to the single-molecule force spectroscopy field. This combination does not only drastically enhance the quality of obtained data, it in fact enables a new class of experiments of biological relevance: the method allows experimentation at high protein density, as found in the cell, but with the resolution and functionality of single-molecule (force-measuring) techniques. This new capability allows the method to bridge the gap between idealized single-molecule experiments and realistic in vivo experiments. This important combination of research fields can form the future of quantitative biological research focused on unravelling the complete and detailed functioning of cellular processes.

Combining force spectroscopy with super-resolution nanoscopy represents a step which can link biophysics to biology. This link can extend the biological relevance and impact of the field e.g. because: (i) STED microscopy can allow imaging of single proteins on DNA in buffer with protein concentrations that are comparable to the concentrations of many DNA-associated proteins in cells; (ii) STED nanoscopy can allow resolving individual proteins on DNA that are separated less than the diffraction limit. This overcomes the need to apply the artificial single-molecule conditions of sparsely coated DNA to distinguish individual proteins; (iii) STED nanoscopy on optically stretched DNA provides high time resolution. 1D scanning along DNA with the photon-efficient super-resolution technique STED allows observing fast spatial dynamics of DNA-protein interactions. The method opens up many exciting opportunities to quantitatively unravel essential biological processes such as DNA replication, DNA organization, and DNA repair, in biologically relevant conditions. In conclusion, the method provides a conceptual and methodological milestone in life-sciences research that can lead to quantitative and more realistic insights in the functioning of cells.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1B:
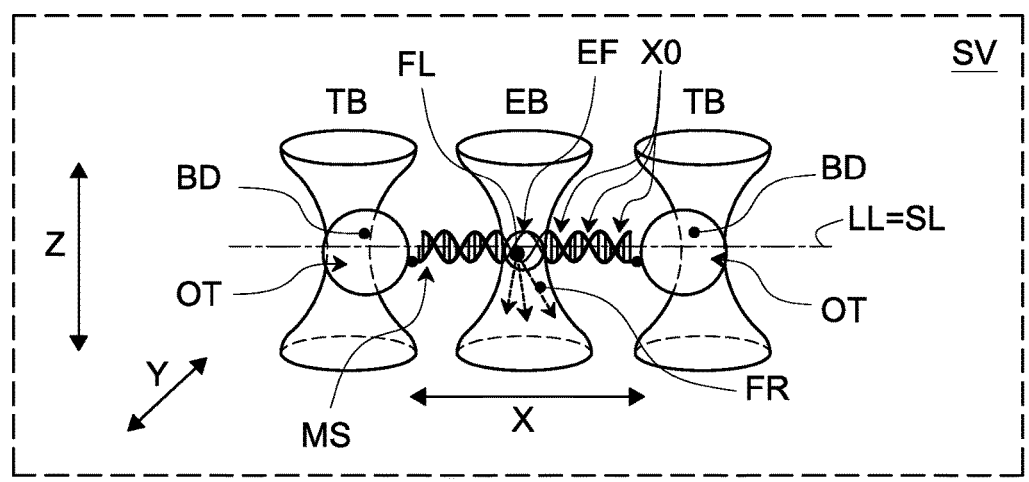
FIG. 1B shows an illustration of the strand held by optical traps.
Figure 2:
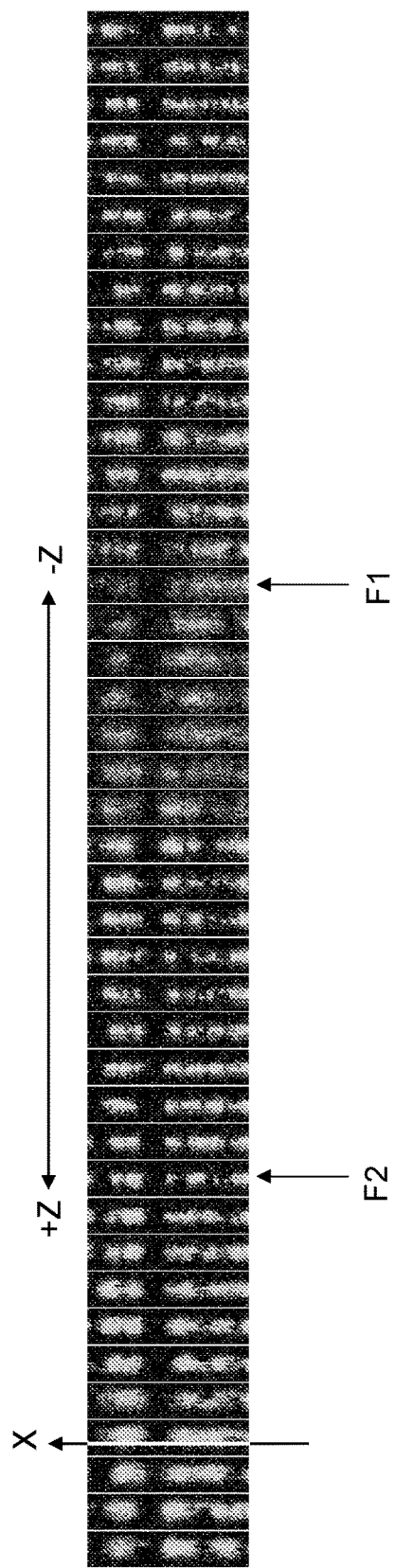
FIG. 2 illustrates fluorescent images for aligning the strand.

FIG. 1A illustrates an embodiment of a system and method for imaging a molecular strand. FIG. 1B shows an illustration of the molecular strand MS.

The method comprises providing a sample volume SV comprising the strand MS. The method further comprises providing an excitation beam EB having an excitation focus EF in the sample volume SV wherein an excitation of a fluorophore FL on the strand MS by the excitation focus EF results in a fluorescence response FR when the excitation focus EF coincides with the fluorophore FL. The method further comprises scanning the excitation focus EF in the sample volume SV along a one dimensional scanning line SL. The method further comprises trapping an end of the strand MS in the sample volume SV and extending the strand MS along a one-dimensional trapping line LL parallel to the scanning line SL. The method further comprises aligning the trapping line LL to coincide with the scanning line SL to have the scanning excitation focus EF coincide with the strand MS. The method further comprises recording the fluorescence response FR as a function of a plurality of distinct scanning positions X0 of the excitation focus EF along the scanning line SL.

In one embodiment, the method further comprises providing a depletion beam DB having a depletion focus DF with a depletion profile coinciding with an excitation profile of the excitation focus EF and causing stimulated emission depletion STED of the excitation of the fluorophore FL according to the depletion profile. The depletion profile has a minimum intensity at a centre of the excitation focus EF for reducing a profile size of the excited fluorophores (i.e. the emission profile of spontaneous fluorescence) by the stimulated emission depletion STED. Stimulated emission depletion (STED) microscopy is a process that provides super resolution by selectively deactivating fluorophores. In this way the diffraction limit of conventional microscopy can be bypassed to achieve better resolution.

In one embodiment, the method comprises providing optical traps OT trapping beads BD attached on opposite ends of the strand MS. The optical traps OT are arranged to form the trapping line LL between the beads BD and may be used to facilitate the aligning of the trapping line LL to coincide with the scanning line SL.

In one embodiment, the beads BD have a diameter larger than the waist of the trapping laser, typically more than 2 µm, preferably more than 3 µm. The relatively large beads i.e. microspheres can be advantageously used to spatially separate the fluorescent labels on the strand MS, e.g. DNA-protein complexes from the trapping beams TB. This separation can prevent photo-bleaching due to the simultaneous presence of fluorescence excitation and trapping beams. Alternatively or in addition also temporal separation between the trapping beams TB and excitation beam EB can be used, i.e. the trapping beams TB and excitation beam EB can be alternatingly switched on and off in counter phase with respect to each other as described e.g. in WO2007/038260. Alternatively, or in addition, photo-bleaching can be reduced by use of triplet relaxation approaches and/or the use of reductive-oxidative system (ROXS) buffers.

In one embodiment, the fluorescence response FR is recorded at an image plane IP. The image plane IP is a conjugate focal plane OP* of an object plane OP in the sample volume SV. The object plane OP extends in the first direction X and a second direction Y. The excitation focus EF and trapping line LL are aligned to coincide with the object plane OP. A spatial pinhole is provided in the image plane IP. The spatial pinhole is aligned to coincide with a conjugate focal point EF* of the excitation focus EF for passing the fluorescence response FR through the spatial pinhole to a fluorescence detector FD.

The object plane OP of a microscope is a conjugate focal plane of an image plane IP of the microscope, i.e. where the image of the object is recorded. In optics, a conjugate focal plane of a given plane, OP, is a plane OP* such that points on OP are imaged at OP*. By placing a spatial pinhole in the image plane, light that is not originating from the object plane, i.e. away from the focal plane of the point focus can be filtered. In this way a better depth discrimination (Z) can be achieved.

By using point focus illumination, a specific part of the sample volume is illuminated, e.g. compared to wide field illumination. In this way a higher signal can be obtained due to a higher intensity at the focus and/or the resulting signal can be correlated to position of the focus. In the present examples, a fluorophore is illuminated by excitation light that is focussed on the molecular strand. Alternative to fluorescence, also other (optical) mechanisms and microscopy methods may be employed for probing the strand by means of point focus illumination, e.g. involving Raman spectroscopy such as CARS (coherent anti-stokes Raman spectroscopy) microscopy. Alternatively or in addition non-linear optical processes can be used, e.g. two-photon excitation.

Confocal microscopy typically comprises using point focus illumination of the sample volume and a spatial pinhole placed in the conjugate focal plane of the point focus. This configuration can improve the image resolution and depth discrimination. While confocal microscopy is typically used to scan and reconstruct three-dimensional structures, the present disclosure provides a one-dimensional scanning of the strand MS.

In one embodiment, the excitation focus EF is repeatedly scanned back and forth along the scanning line. The fluorescence response FR can be distinguished between the plurality of distinct scanning positions X0 along the scanning line SL and integrated over multiple scans and/or recorded as a function of time.

The method can be executed by a system for imaging a molecular strand MS. The system comprises a sample cell SC arranged for providing a sample volume SV comprising the strand MS. The system further comprises an excitation light source EL arranged for providing an excitation beam EB having an excitation focus EF in the sample volume SV wherein an excitation of a fluorophore FL on the strand MS by the excitation focus EF results in a fluorescence response FR when the excitation focus EF coincides with the fluorophore FL. The system further comprises a beam scanner M3 arranged for scanning the excitation focus EF in the sample volume SV along a one dimensional scanning line SL. The system further comprises a trap TL arranged for trapping an end of the strand MS in the sample volume SV and extending the strand MS along a one-dimensional trapping line LL parallel to the scanning line SL. The system further comprises a beam aligner (e.g. formed by steering mirror M3 in conjunction with telescopes T1 and/or T3) arranged for aligning the trapping line LL to coincide with the scanning line SL to have the scanning excitation focus EF coincide with the strand MS. The system further comprises a fluorescence detector FD arranged for recording the fluorescence response FR as a function of a plurality of distinct scanning positions X0 of the excitation focus EF along the scanning line SL. The system further comprises a computer processor CPU programmed to provide a scanning mode.

In the scanning mode the processor CPU controls the trap TL to extend the strand MS along a one-dimensional trapping line LL in the first direction X. Ian the scanning mode the processor controls the beam aligner to have the trapping line LL coincide with the scanning line SL. In the scanning mode the processor controls the beam scanner M3 to scan the excitation focus EF along the scanning line SL. In the scanning mode the processor receives the recorded fluorescence response FR from the fluorescence detector FD. In the scanning mode the processor stores the fluorescence response FR as a function of a position X0 of the excitation focus EF along the scanning line SL.

The program for executing the said instructions can e.g. be stored in a memory that is accessible to the processor. The memory can e.g. be random accessible memory and/or a data carrier. In one embodiment there is provided a computer storage medium encoded with a computer program, the program comprising instructions that if executed by one or more computers linked to a system as described, cause the one or more computers control the system to perform operations comprising one or more methods as described herein, e.g. the scanning of the molecular strand, and/or aligning of the molecular strand.

In one embodiment, the system further comprises a depletion light source DL and depletion beam optics M3,T3. The depletion light source DL and depletion beam optics M3,T3 are arranged for providing a depletion beam DB having a depletion focus DF with a depletion profile coinciding with an excitation profile of the excitation focus EF and causing stimulated emission depletion STED of the excitation of the fluorophore FL according to the depletion profile. The depletion profile has a minimum intensity at a centre of the excitation focus EF for reducing a size of the profile of excited fluorophores by the stimulated emission depletion STED.

In one embodiment, the system comprises a depletion focus shaper PP arranged for shaping the depletion profile wherein the depletion profile comprises a plane of minimum intensity extending perpendicular to the trapping line LL. The depletion focus shaper PP may e.g. comprise a phase plate arranged in the depletion beam DB for shaping the depletion focus profile e.g. as explained in an article by Klar et al. (Physical Review E, Volume 64, 066613, "*Breaking Abbe's diffraction resolution limit in fluorescence microscopy with stimulated emission depletion beams of various shapes*"). Also other means besides a phase plate for achieving a line or plane shaped STED focus profile can be envisaged, e.g. crossing two coherent STED beams from different directions to provide a line shaped interference pattern between the beams.

In one embodiment, the trap comprises a trapping light source TL and trapping beam optics (e.g. telescope, rotatable mirrors, trapping beam detectors) arranged for providing optical traps OT trapping beads BD attached on opposite ends of the strand MS. In use, the optical traps OT can be arranged along the first direction X to form the trapping line LL between the beads BD. The processor is programmed to provide an alignment mode. In the alignment mode, the processor controls the beam scanner and trap and receives from the fluorescence detector (FD) a first fluorescence image of the strand MS by scanning the excitation focus EF in an object plane OP. In the alignment mode, the processor controls moving the optical traps OT relative to the scanning line SL in a direction Z perpendicular to the object plane. The processor then receives from the fluorescence detector FD a second fluorescence image of the strand in the object plane OP. The processor (CPU) compares the first and second fluorescence images and is programmed to repeat moving the trapping line LL relative to the scanning line SL in the same direction Z when the second fluorescence image compared to the first fluorescence image has a decreased line thickness of the strand MS and/or a higher contrast. In principle, for aligning in the Z direction, scanning is not necessary, e.g. a fixed X,Y position can be used on the DNA strand and the intensity maximized.

A fluorophore (or fluorochrome) is a fluorescent chemical compound that can re-emit light upon light excitation. The fluorophore typically absorbs light energy of a specific wavelength and re-emits light at a longer wavelength. In one embodiment, the molecular strand comprises and/or binds to a fluorophore to provide convenient visualization of the strand. In one embodiment, a fluorescent staining solutions is used to stain the molecular strand. One example of a staining solution is SYTOX® Green. SYTOX® Green nucleic acid stain (CAS number: 194100-76-0) is a high-affinity nucleic acid stain. Another example is SYTOX® Orange. Also other DNA stains or intercalating dyes can be used, such as fluorescent proteins (such as GFP, YFP, mCherry), quantum dots, nano diamonds, organic dyes (such as those of the Alexa Fluor, Attotec, or Cy-dye series). For example, after brief incubation with SYTOX® Green nucleic acid stain, the nucleic acids fluoresce bright green when excited e.g. with a 450-490 nm light source. Advantageously it has a >500-fold fluorescence enhancement upon nucleic acid binding. Also other known or to be developed staining solutions can be used. Alternatively or in addition to a staining solution, the molecular strand may also be fluorescent itself, e.g. comprise one or more fluorescent parts. Alternatively or in addition fluorescent reactants to be studied, e.g. fluorescent proteins, may bind to the molecular strand. The strand may thus be imaged directly through its own fluorescence or indirectly by fluorescent molecules including fluorophores binding thereto.

In the shown embodiment, beams TB, EB, FR, and DB are combined or split up using dichroic mirrors D1, D4, D7. Of course also other means can be used for combining/splitting the beams, e.g. fibres and/or diffracting/refracting optics such as prisms and gratings. In the shown embodiment, the trapping beams TB are detected by trapping beam detector TD, e.g. for determining a force exerted on the strand. Such detector may also be omitted or switched off once the strand is trapped.

In one embodiment, the aligning the trapping line LL to coincide with the scanning line SL comprises recording a first fluorescence image F1 of the strand MS by scanning the excitation focus EF in an object plane X,Y; moving the trapping line relative to the scanning line in a direction +Z perpendicular to the object plane X,Y; and recording a second fluorescence image F2 of the strand the object plane X,Y. In one embodiment the first and second fluorescence images F1,F2 are compared; and the trapping line LL is moved again relative to the scanning line SL in the same direction +Z when the second fluorescence image F2 compared to the first fluorescence image F1 has a decreased line thickness of the strand MS and/or a higher contrast. Alternatively, the trapping line LL is moved again relative to the scanning line SL in an opposite direction −Z when the second fluorescence image F2 compared to the first fluorescence image F1 has an increased line thickness of the strand MS and/or a lower contrast.

The line thickness can be calculated e.g. as the full width half maximum (FWHM) of the fluorescence response FR as a function of a coordinate Y transverse to the length direction X of the strand MS in the fluorescence images F1,F2. The fluorescence response FR can be optionally integrated across multiple coordinates X of the strand MS for improving the accuracy. Also other metrics can be used for evaluating the line thickness, e.g. a standard deviation. The thickness can also be calculated by fitting the fluorescence to a profile, e.g. Gaussian fit.

In one embodiment, the contrast can be calculated by examining a derivative of the fluorescence response FR along any direction of the image, e.g. X and/or Y. Typically, a higher contrast results in a higher derivative. Also other methods for calculating a contrast and/or line thickness can be used. Alternatively or in addition, also a maximum and/or integrated fluorescence response FR can be used as a measure of the alignment. For example, a higher maximum and/or total fluorescence response FR of the strand MS may correspond to a better alignment. In one embodiment, the strand is aligned by maximizing absolute pixel brightness.

In one embodiment, in order for the confocal/STED imaging plane to match with the plane where the molecular strand is placed, the position of a lens in the telescope T1 (FIG. 3A) can be controlled by using a motorized stage. By moving the lens along the optical axis of the trapping laser it is possible to move the position of the optical traps and therefore of the microspheres and the molecular strand within the sample. Typically, the DNA is the molecular strand and a fluorescent chemical such as SYTOX-orange is used for visualization. In one embodiment, the sample is illuminated and images of the molecular strand are acquired while the lens of the optical trap is moved to displace the molecular strand in the z-direction. The width-profile at each lens displacement is analysed. In one embodiment, when the z-plane of the DNA and the imaging plane of the apparatus coincide a minimum of the width is observed.

Figure 3A:
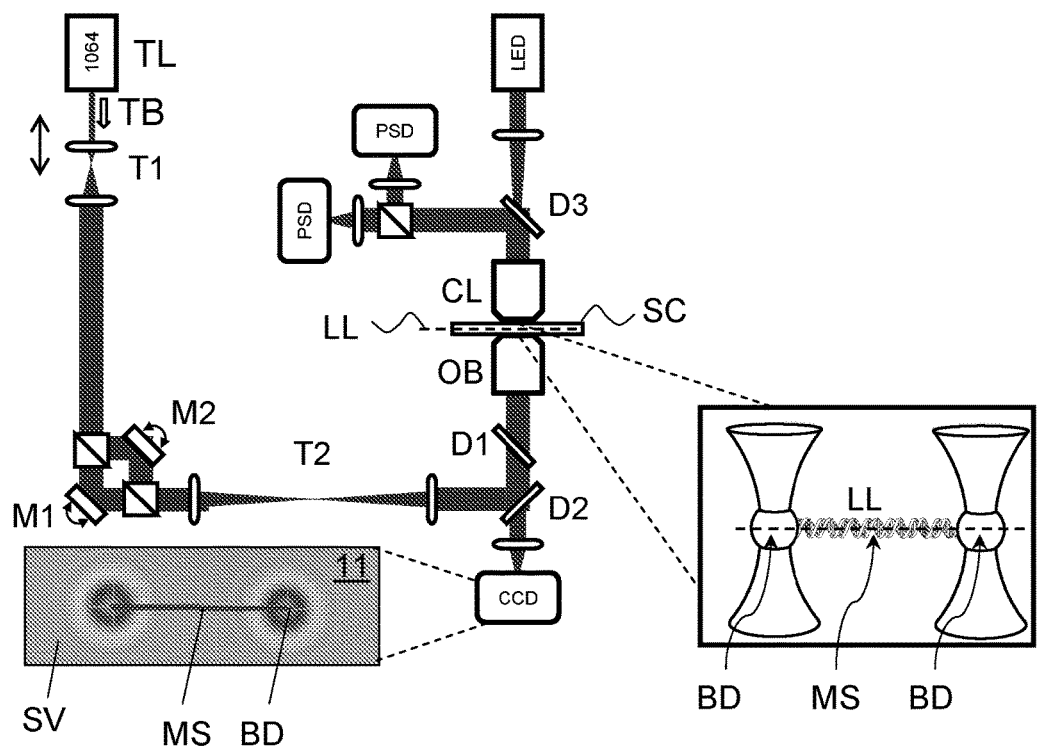
FIG. 3A shows an embodiment of an optical tweezers instrument

FIG. 3A shows an embodiment of an optical trap for trapping the molecular strand in the sample volume. The present embodiment provides optical tweezers to trap an end of the strand MS. Optical tweezers use a focused laser beam (the optical trap) to provide an attractive or repulsive force, depending on the refractive index mismatch to hold and move a microscopic object, typically a dielectric microsphere or bead BD.

The present embodiment provides a trap light source TL to provide a trap beam TB. In this case the trap light source TL has a wavelength of 1064 nm, but also other wavelengths may be used. Preferably, the wavelength is chosen to minimally interfere with the excitation of the fluorophore. The beam TB enters a first telescope T1 to enlarge the beam. The beam is split in two polarizations, e.g. using polarizing cubes. By using separate polarizations for the two trapping beams TB, these can be distinguished and measured separately behind the sample. The two polarizations hit separate rotation controllable beam steering mirrors M1 and M2. The two polarized beams are recombined and sent into a second telescope T2. The second telescope T2 may lessen angle variations of the beams that can result from the beam steering mirrors M1 and M2. It is noted that the telescope images the steering mirrors onto the backfocal plane of the objective. Rotating the mirrors will therefore lead to only an angle change (pivoting) of the beam through the objective (not a position change). In this way homogeneous scanning of the sample can be achieved. The first and/or second telescopes T1,T2 can also be used to collimate the trapping beams and/or change a position of the focal plane of the trapping beams in the sample volume SV, e.g. by moving a lens of telescope T1 as indicated by the arrow. In this way the position of the trapping line LL in the sample volume SV can be adjusted in a Z direction by one or both of the telescopes T1,T2 while an X and/or Y direction can be adjusted by the beam steering mirrors M1 and M2.

After the second telescope T2, the trapping beams are reflected by dichroic mirror D2 and transmitted by dichroic mirror D1 to be focussed in the sample at the trapping line LL or focal plane by objective lens OB and re-collimated after the sample by condenser lens CL. The trapping beams are then redirected by dichroic mirror D3 and re-split into separate polarizations to be projected on position sensitive devices (PSD). In one embodiment, a position sensitive device (PSD) is an optical position sensor, that can measure a position of a light spot in one or two-dimensions on a sensor surface. In one embodiment, a position of the beads BD is determined using back-focal-plane (BFP) interferometry. In BFP interferometry, light scattered by the bead interferes with the other light of the trapping beam in the back-focal-plane of the condenser (e.g. condenser lens CL). A position of the bead in the trap can be inferred from this interference pattern on the detector. From the position of the bead in the trap, a force exerted on the bead can be calculated. In an embodiment where the beads are larger than the focus, all the light travels through the bead and the bead works as a lens and displaces the (total) beam if it is displaced from the trapping focus.

Alternatively or in addition to the BFP detection, the beads can also be imaged using a regular lighting and camera. For example, in the shown embodiment, an LED light source is used to illuminate the beads and the resulting picture is imaged on a CCD camera as shown by the inset picture 12.

Figure 3B:
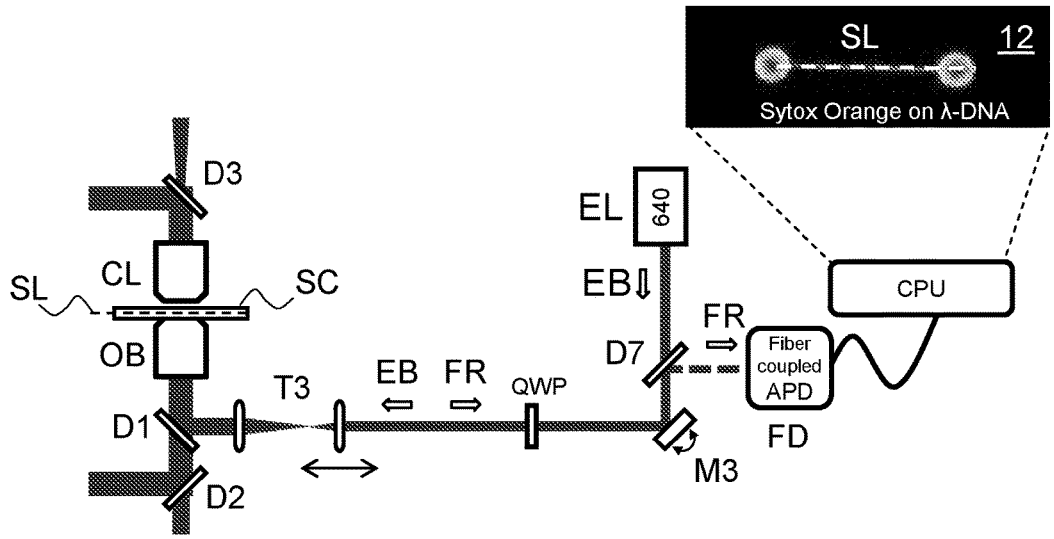
FIG. 3B shows an embodiment of a confocal microscope.

FIG. 3B shows an embodiment of a confocal microscope. An excitation light source EL provides an excitation beam EB. In the present example the excitation beam EB has a wavelength of 640 nm. Alternatively also other wavelengths can be used e.g. dependent on an excitation wavelength of a specific fluorophore to be imaged. The excitation beam EB is transmitted by dichroic mirror D7 and directed to beam steering mirror M3. Optionally, a quarter wave plate QWP is inserted in the beam to provide a circularly polarized beam. The excitation beam EB enters telescope T3 that can be used to increase the beam diameter and/or change a focal position of the excitation focus in the sample, e.g. by moving a lens of the telescope T3 as indicated by the arrow. Alternatively or in addition, the collimating can be done at a fibre out coupling. In this way e.g. different colors/beams can be collimated independently. The excitation beam EB is reflected towards the objective lens OB by dichroic mirror D1. It is noted that this same dichroic mirror may transmit the trapping beams TB and/or the light from the LED shown in FIG. 3A. The excitation beam EB is focussed in the sample volume to form an excitation focus. The excitation focus can be scanned in the sample volume e.g. by a beam scanner, in this case by the beam steering mirror M3.

When the excitation focus overlaps with a fluorophore, a fluorescent response FR can be emitted from the fluorophore. In the present embodiment, (part of) the fluorescence response FR travels back through the system until it meets dichroic mirror D7 which reflects the fluorescence response beam into a fluorescence detector FD. In this case the fluorescence detector FD comprises an avalanche photodiode (APD). An APD is a highly sensitive semiconductor electronic device that exploits the photoelectric effect to convert light to electricity. Alternatively or in addition to an APD, also a photomultiplier tube (PMT, not shown here) could be used. A PMT multiplies current produced by incident light, in multiple dynode stages, enabling (for example) individual photons to be detected when the incident flux of light is low. In one embodiment, the fluorescence detector FD is fibre coupled. In one embodiment, a lens (not shown) is provided in front of the fibre to couple the fluorescence response light into the fibre. An input aperture of the fibre may function to reject out of focus light, i.e. light not originating from the focal plane of the excitation focus. In this way the fibre entrance may operate similar to a pinhole in a confocal microscope setup.

The fluorescence detector FD is connected to a computer CPU which records the fluorescence response signal. In addition, the computer CPU may also directly or indirectly control one or more of the beam steering optics, e.g. beam scanner M3 and or a lens of telescope T3, to move the excitation focus in the sample volume SV. In a scanning mode the processor CPU may e.g. be programmed for controlling the beam scanner M3 to scan the strand MS along the scanning line SL and record the fluorescence response FR as a function of a scanning position, corresponding to a molecular position on the strand MS.

Figure 4A:
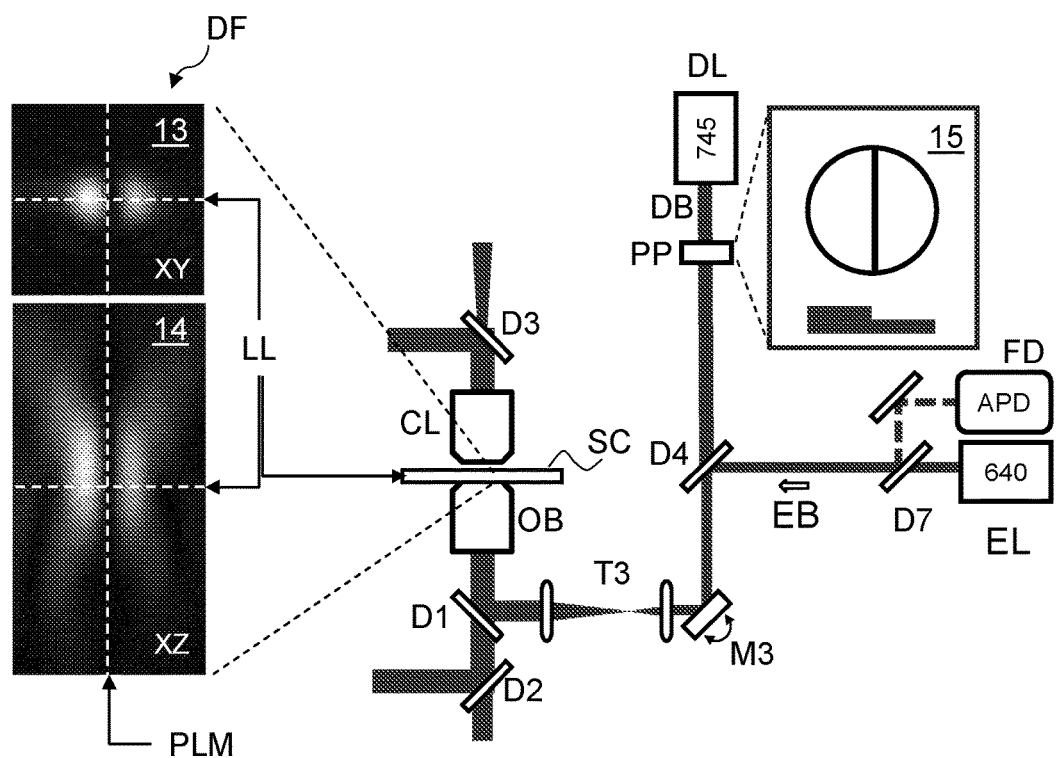
FIG. 4A-B show a embodiments for performing STED.
Figure 4B:
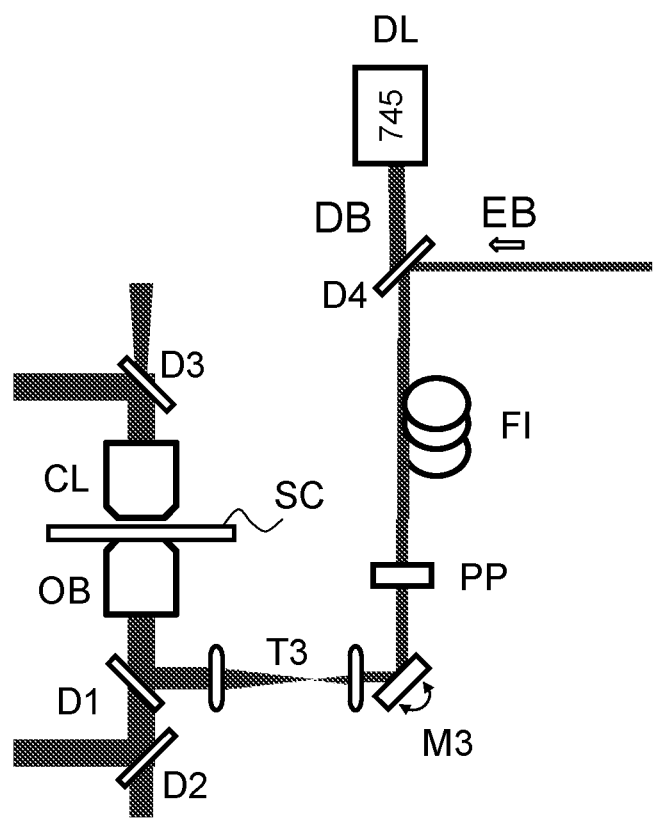

FIG. 4A shows a first embodiment for performing stimulated emission depletion (STED). FIG. 4B shows a second embodiment for performing stimulated emission depletion (STED). In the STED embodiments, a depletion light source DL is added e.g. to provide a depletion beam DB. In the embodiment of FIG. 4A only the depletion beam DB is transmitted through a phase plate PP. In the embodiment of FIG. 4B, the excitation beam EB and depletion beam DB are sent through a fibre FI to align the beams. In this embodiment, both beams are sent through a phase plate PP. The phase plate PP can e.g. be constructed to retard with one half of the phase plate PP, the depletion beam DB wavelength by half a wavelength while retarding the wavelength of the excitation beam EB by an integer number of wavelengths. In other words, half the beam is retarded half a wavelength with respect to the other half of the beam (both are retarded but with a difference of half a wavelength.

The depletion beam DB e.g. has a wavelength of 745 nm or any other wavelength suitable for stimulating depletion of the fluorophores that are brought to an excited state by the excitation beam EB. The depletion beam DB results in a depletion focus DF which is overlapped with the excitation focus to promote stimulated emission before the excited fluorophores emit the fluorescence response. Typically the excitation beam EB and depletion beam DB comprise pulsed light. Preferably, the light pulses of the depletion beam DB are delayed with respect to those of the excitation beam EB but within the fluorescent lifetime of the fluorophores to spontaneous fluoresce emission.

In one embodiment, the depletion focus comprises a line shaped minimum intensity profile oriented perpendicular to the trapping line LL. In one embodiment, e.g. as shown in the inset pictures 13 and 14, the depletion profile of the depletion focus DF comprises a plane of minimum intensity PLM extending perpendicular to the trapping line LL, i.e. the minimum intensity extends in the Y and Z directions. The plane or line shaped depletion profile PLM has two-fold symmetry (two "lobes") in XY as opposed to the circular symmetry of e.g. a donut profile. The depletion profile PLM also has two-fold symmetry in XZ. In one embodiment, the plane of minimum intensity is curved, e.g. moon-shaped.

Where the depletion profile has minimum intensity, the depletion of the excited molecules is minimal. In other words, the remaining excitation profile, after depletion, is reciprocal to the depletion profile. For the present depletion profile with a plane of minimum intensity PLM, this means that excitation of the molecules will be minimally depleted along said plane PLM. It will be appreciated that because the plane of minimum intensity PLM extends perpendicular to the trapping line LL, spatial thermal fluctuations of the strand within the plane PLM will have less effect on the measured emission. By increasing the intensity of the depletion focus DF, the valley of the minimum intensity PLM can be narrowed. Without being bound by theory, the non-linear dependence of the remaining emission profile of the fluorophores on the intensity of the depletion profile can be used for overcoming the diffraction barrier.

In one embodiment, a plane of minimum intensity PLM is obtained by destructive interference between two halves of a beam or two beams along a line in the focus (perpendicular to the trapping line LL). In one embodiment, the destructive interference is achieved by phase shifting one of the two halves by 180 degrees. In one embodiment, a phase front of a depletion beam DB is split in two portions by means of a phase plate PP. The phase plate PP provides a relative phase shift between the two halves of 180 degrees. For example, the phase plate PP comprises two halves wherein one half retards the phase front more than the other half. The phase plate can be based e.g. on refraction and/or reflection. Inset picture 15 shows a top and side view of an embodiment of a phase plate PP. One half of the phase plate is thicker than the other half. The difference in thickness may e.g. corresponds to a retardation of half a wavelength of the light of the excitation beam EB through the phase plate PP.

Figure 5A:
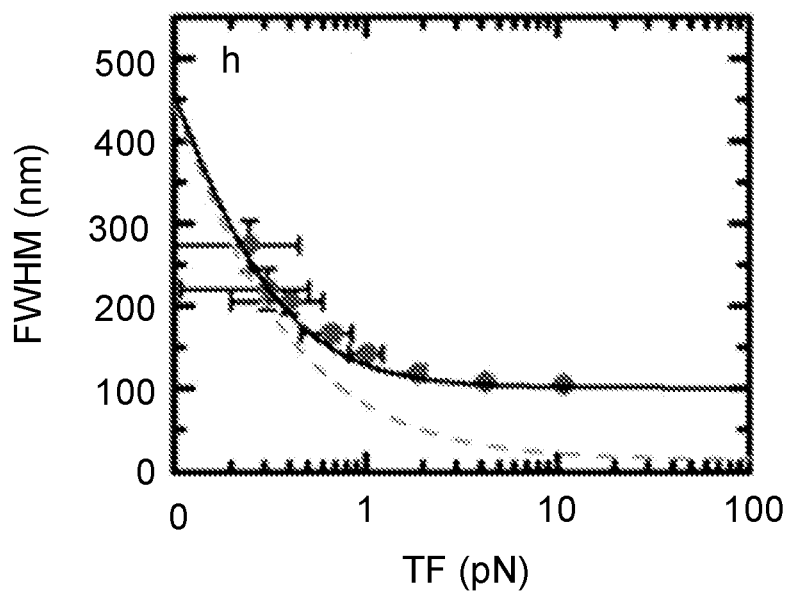
FIG. 5A-B illustrate the influence of tension force on imaging resolution using STED.

FIG. 5A shows a measurement of the FWHM of a fluorophore signal as a function of the tension force TF of the strand, in this case the average FWHM of Gaussian fits to intensity profiles obtained from individual BsoBI-Atto647N restriction enzymes on DNA. This figure demonstrates the importance of control of the tension on the strand to achieve high resolution imaging. For example, thermal fluctuations of suspended DNA can blur the images taken of DNA-bound proteins. However, the amplitude of such fluctuations can be reduced by applying tension to the DNA using optical tweezers. The figure shows the measured FWHM of images of single fluorophores as function of applied tension force TF, revealing a loss of effective resolution at forces below ~5 pN. The data points are described by a model (line) that convolves the optical resolution with estimated longitudinal DNA fluctuations. The calculated fluctuations are indicated by the dashed line.

Figure 5B:
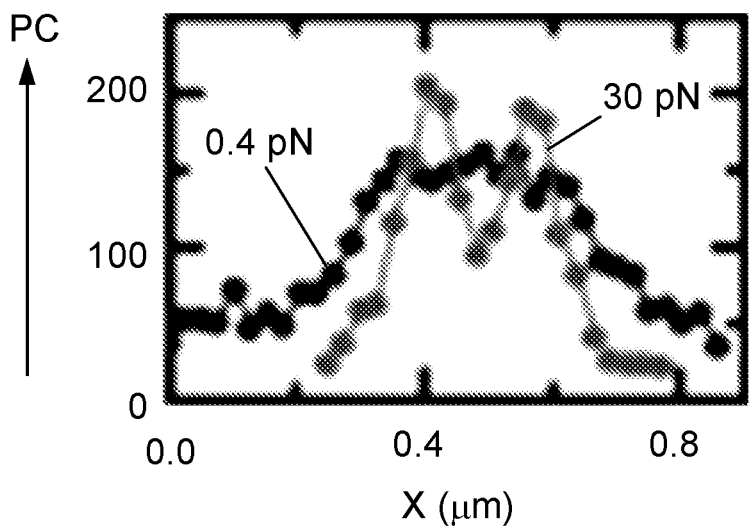

FIG. 5B shows a STED enhanced scan of the fluorescence response from a strand held by beads at two different tension forces on the strand (DNA), 0.4 pN and 30 pN. In particular the figure shows the photon count PC as a function of molecular position X in μm (micrometers). This figure illustrates that reducing the DNA tension from 30 pN down to 0.4 pN completely abolishes the ability of STED nanoscopy to resolve two DNA-bound proteins in close proximity. Accordingly, in one embodiment optically trapped beads are attached to the strand for trapping the strand, wherein the beads exert a tensile force on the strand larger than 5 pN, preferably larger than 10 pN. In one embodiment, the tensile force is applied by flow-stretching, e.g. in combination with one trapped bead.

Figure 6A:
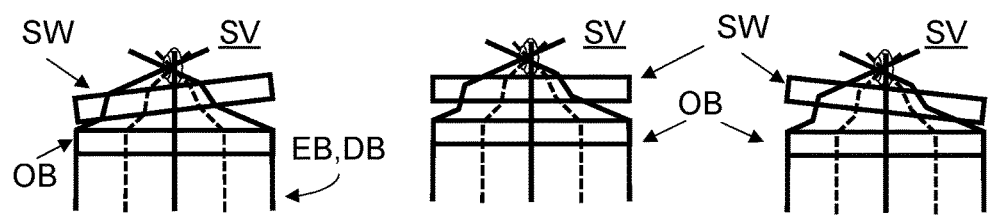
FIG. 6A-C shows the effects of tilting a sample window.
Figure 6B:
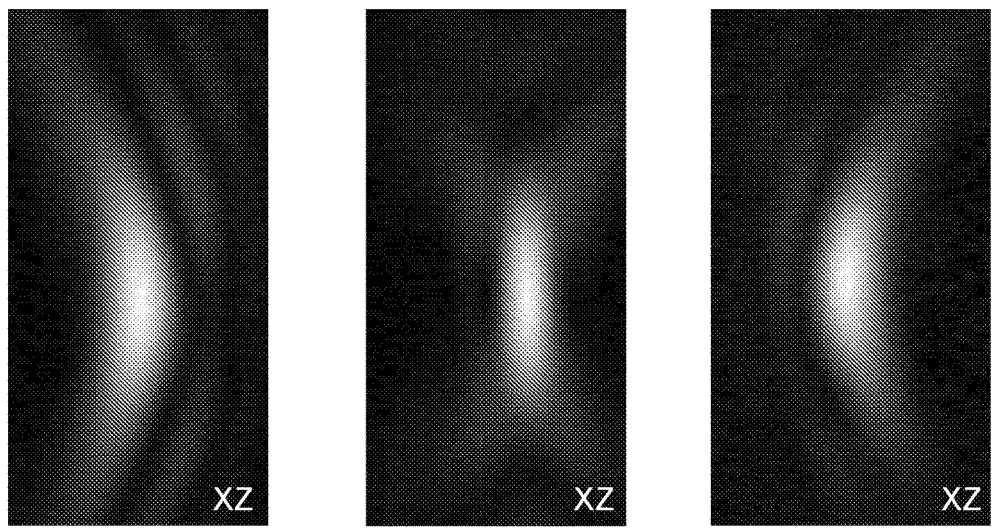
Figure 6C:
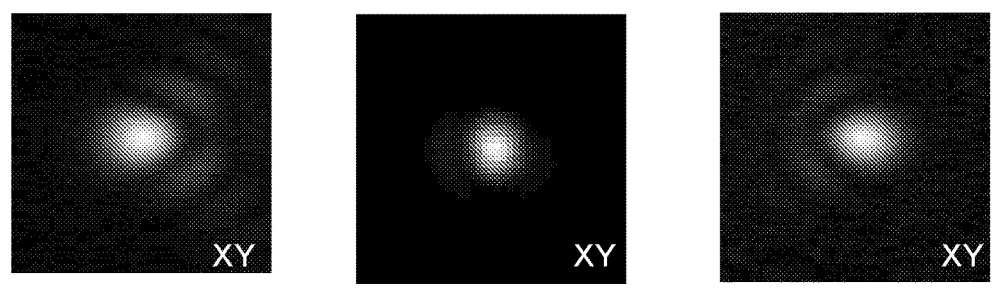

FIG. 6A shows an arrangement of a sample window SW containing a sample volume SV tilted at three different angles, e.g. with respect to the incoming excitation beam EB and/or depletion beam DB focussed by the objective lens OB. FIG. 6B shows the resulting excitation focus in the XZ plane for the three respective arrangements of FIG. 6A. FIG. 6C shows the resulting excitation focus in the XY plane for the three respective arrangements of FIG. 6A. It can be observed that if the sample window SW is improperly tilted with respect to the incoming beams, the excitation profile size and/or shape may deteriorate. The images are made by using gold beads in an agarose matrix.

In one embodiment, the sample volume SV is comprised in a sample cell comprising a sample window SW transparent to incoming excitation and/or depletion beams DB,EB. A position of the sample cell is driven by rotational actuators (not shown). The embodiment further comprises aligning the sample window SW to be perpendicular to the incoming beams DB,EB for optimizing a profile of the excitation focus and/or depletion focus.

In one embodiment, the microfluidic flow cell is connected to a motorized stage with the ability to move linearly in three independent dimensions and rotate around two independent axes. The possibility of moving the stage in three dimensions with respect to the trap position is desired for performing a catch and measure approach such as illustrated in FIG. 7B, wherein the flow cell can be moved while the traps are held in place. The possibility of rotating the axis around two axes is desired for the STED integration. In particular, for STED is desired that the optical axis of the incoming STED laser beam is perpendicular to the bottom glass slide of the microfluidic chip as discussed above. In one embodiment, the molecular strand, the spherical objects and one or more other chemical reagents are injected in the microfluidic flow cell using separate channels.

Figure 7A:
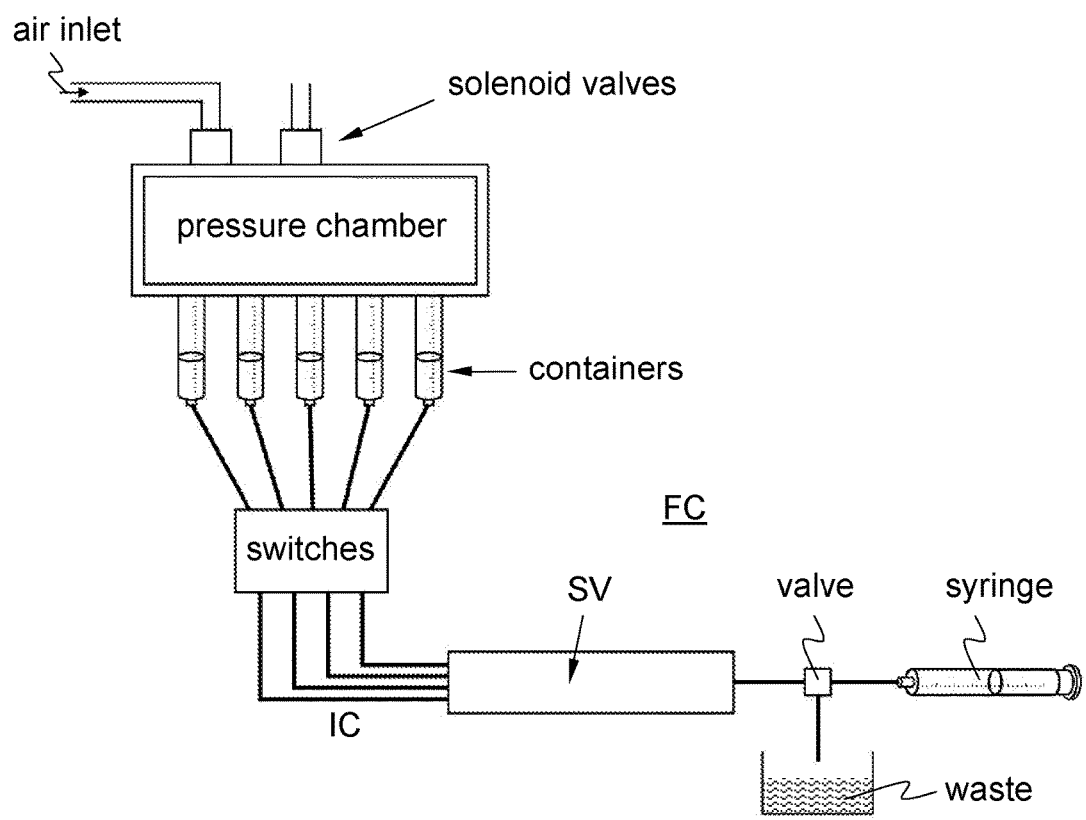
FIG. 7A shows a schematic setup of a flow system.
Figure 7B:
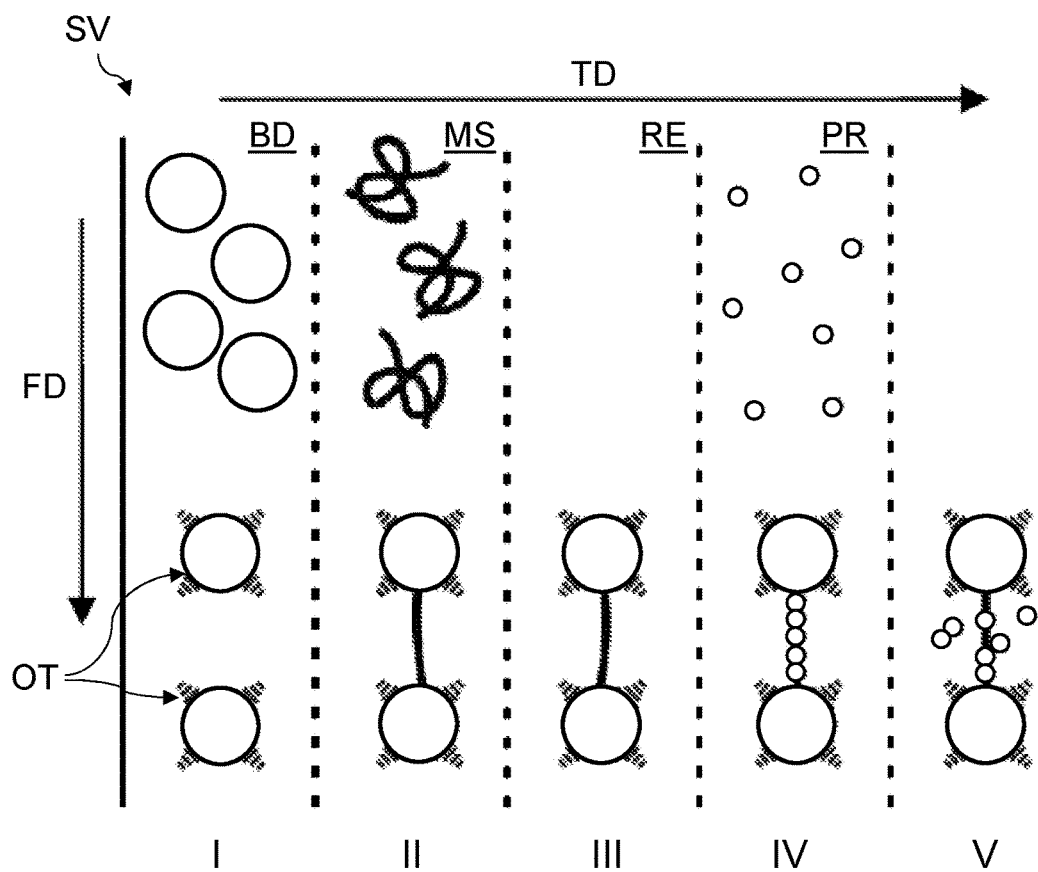
FIG. 7B schematically shows a plurality of separate laminar flows.

FIG. 7A shows a schematic setup of a microfluidic flow cell FC. FIG. 7B schematically shows a plurality of separate laminar flows I-V in a sample volume SV of the flow cell that flow in direction FD. Due to the laminar nature of the flows, contents of adjacent flows typically do not mix.

In one embodiment, the sample cell SC comprises a microfluidic flow cell FC wherein separate input channels IC of the flow cell FC provide a plurality of separate laminar flows I-V in a sample volume SV of the flow cell FC. The trap TL comprises optical traps OT trapping beads BD attached on opposite ends of the strand MS. The optical traps OT are arranged to form the trapping line LL between the beads BD. The optical traps OT are moveable with respect to the laminar flows I-V, e.g. by moving the flow cell. In one embodiment there is provided a method for measuring interaction of a fluorescent reagent with a molecular strand MS. The method comprises providing a microfluidic flow cell FC wherein separate input channels IC of the flow cell FC provide a plurality of separate laminar flows I-V in a sample volume SV of the flow cell FC. A typical arrangement consists in the following. A first laminar flow I comprises a plurality of beads BD arranged for attaching to opposite ends of the molecular strand MS. A second laminar flow II comprises a plurality of the molecular strands MS. A third laminar flow III,IV comprises the reagent RE,PR. The method comprises providing optical traps OT in the first laminar flow I and trapping at least two beads BD with the optical traps OT. The method further comprises moving the optical traps OT to the second laminar flow II and attaching the beads BD to a strand MS. The method further comprises moving the optical traps OT to the laminar flow III and/or IV, and using a method as described herein for recording the fluorescence response FR of the reagent RE and/or PR as a function of molecular position along the strand MS.

In one embodiment, the molecular strand MS is a DNA strand and the fluorescent reagent PR comprises protein molecules that provide a fluorescent signal. Accordingly there is provided a method for measuring interaction of one or more protein molecules with a strand of DNA.

Figure 8:
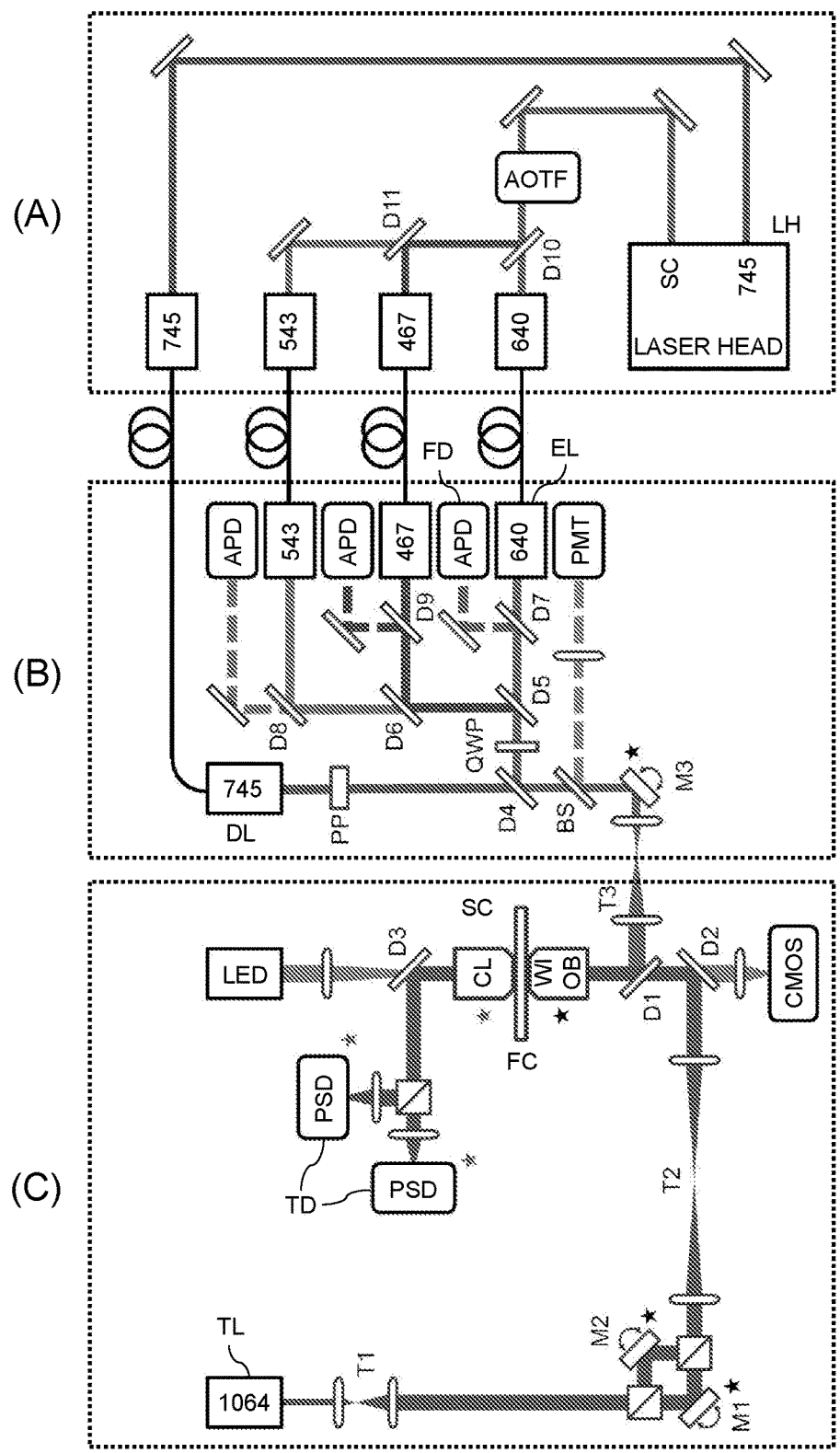
FIG. 8 shows an embodiment of a system that can be programmed for imaging a molecular strand complex.

FIG. 8 shows an embodiment of a system that can be programmed for imaging a molecular strand according to the present disclosed method. The experimental setup shows beam paths and various components. Optical trapping (1064 nm): Two orthogonally polarized optical traps are independently steered using tip/tilt mirrors (M1 and M2) and the force acting on the microspheres (displacement from the trapping beam in the focal plane) are measured on two PSDs, e.g. using back-focal plane interferometry or other imaging techniques. The microsphere-to-microsphere distance is obtained from LED-illuminated CMOS camera images (875 nm). Fluorescence: One laser system supplies STED (745 nm) and excitation beams (640 nm, 543 nm, and 467 nm, respectively, filtered from a super-continuum spectrum (SC) using an acousto-optical tuneable filter AOTF). These beams are fibre coupled and delivered to the confocal tip/tilt piezo mirror scanner (M3) after being combined by dichroics. The de-scanned fluorescence signal (dashed lines) is collected on fibre-coupled APDs, while de-scanned excitation light can optionally be detected using a PMT by placing a pellicle beam splitter (BS) in the common path. A STED stripe is formed by a binary phase plate (PP), and optionally the excitation beams can be circularly polarized using a $\lambda/4$ retarder (QWP). Stars indicate planes conjugate to the objective and condenser back focal plane, respectively. D1-11 are dichroic mirrors and T1-T3 are telescopes.

Beam steering optics M1, M2, M3 can be controlled by a computer (not shown). Also one or more of the lenses forming the telescopes T1, T2, T3 can be controlled by the computer. Also the flow cell can be controlled by the computer. The compute may receive data from one or more of the imaging devices, e.g. the PSDs, the CMOS, the PMTs, and/or the APDs. The computer can be programmed with computer code, e.g. stored in a memory of the computer, which code, when executed, receives data from the system and controls the system and its components to perform a method for trapping, aligning and/or imaging a molecular strand, as described herein.

In one embodiment, the microscope and microfluidics can be as follows. The setup comprises an inverted microscope based on a water-immersion objective (CFI Plan Apo IR 60X WI, Nikon, NA 1.27) placed on a vertical stage MVN80 (Newport Corporation) using an adapter. A 5-channel laminar flow cell (Micronit Microfluidics BV) is mounted on an automated XY-stage (IVIS-2000, Applied Scientific Instrumentation), which allows rapid, in situ construction and characterization of dumbbell constructs (typically, a construct is created in less than one minute), and facilitates swift and complete transfer of the tethered DNA between different flow channels (allowing force spectroscopy and visualization experiments to be performed on >20 DNA molecules per hour). A condenser top lens (P 1.40 OIL S1 11551004, Leica) is placed on top of the flow cell. The flow cell and microspheres are illuminated by an 875 nm LED (LED-1115-ELC-875-19-5, IMM Photonics), and imaged in transmission onto a CMOS camera (DCC 1545M, Thorlabs).

In one embodiment, the optical trapping can be as follows. Optical trapping is performed using a 10 W CW fibre laser (YLR-10-LP, IPG Photonics) with coupled optical isolator. Typically, an output power of 3 W is used to trap two beads. The laser beam is expanded using lenses with focal lengths of 75 mm and 150 mm. Here, the 75 mm lens is placed on an automated linear stage (AG-LS25, Newport) to modify the collimation for aligning the optically stretched DNA with the focal plane of the confocal imaging system. Two polarizing beam-splitter cubes (10BC16PC.9, Newport) are used to split the 1064 nm laser into two independently steerable optical traps and recombine these. One coarse positioning piezo stepper mirror (AG-M100N, Newport), and one accurate piezo mirror (Nano-MTA2X Aluminium, Mad City Labs) is used for beam steering the two traps. Two 300 mm lenses couple the trapping beams into the objective. Force measurements are performed by back-focal plane interferometry of the condenser lens using two position sensitive detectors (DL100-7PCBA3, Pacific Silicon Sensor) after separating the two polarized beams using a polarizing beam splitter cube. Two dichroic mirrors (950DCSP, Chroma Technology Corporation) separate the trapping light from the LED illumination before and after the flow cell.

In one embodiment, the confocal and STED fluorescence microscopy can be as follows. A single laser system (ALP-710-745-SC, Fianium Ltd, Southampton, UK) is used for fluorescence excitation and STED. This turn-key system simplifies the implementation of (dual-color) STED and provides flexibility in excitation wavelength. Three excitation bands are selected (centred at 467 nm, 543 nm, and 640 nm, compatible with a range of conventional fluorescent dyes) from a super-continuum spectrum. After polarizing (Glan-Thompson prism PGT 1.08.05, Bernhard Halle Nachfl. GmbH) and filtering the super-continuum spectrum using an AOTF (AOTFnc-VIS-TN, AA Opto-Electronic) the three beams are separated and filtered using appropriate dichroic mirrors (F43-088 and F43-093, AHF Analysentechnik GmbH) and filters (F94-640, F94-543, and F34-467, AHF). The three excitation beams and the STED beam are coupled into single-mode fibres (PMC-640 and PMC-460, Schäfter & Kirchoff GmbH) using laser beam couplers (60SMS-1-4-M15-26 and 60SMS-1-4-M15-37, Schäfter & Kirchoff), and collimated again (collimator 60FC-L-4-M20L-02, Schäfter & Kirchoff or f=20 mm achromats G052006000, Qioptiq). Fine adjustment of the polarization angle of the 745 nm beam before fibre coupling is done using an achromatic $\lambda/2$-retarder (RAC 4.2.10 L, Bernhard Halle). The four beams are combined using dichroic mirrors (F48-533, F33-632, and F73-726, AHF). Beam scanning using a fast tip/tilt piezo mirror (S-334.1SD, Physik Instrumente GmbH & Co) is followed by 1:3 beam expansion and combining with the trapping laser using a dichroic mirror (F43-800, AHF). All (dichroic) mirrors that encounter the STED beam are at least 6 mm thick and have flatness better than $\lambda/10$. The STED beam passes a flat glass window with one halve featuring a coating providing a 180° phase step. In the sample, the resulting focal intensity distribution ideally exhibits zero intensity at the centre of the focus such that saturated stimulated emission only occurs in the high-intensity periphery of the STED beam. 12 For confocal microscopy, the excitation beams can be circularly polarized using a $\lambda/4$-retarder (RAC 4.4.10, Schäfter & Kirchoff). For confocal detection, the emitted fluorescence is de-scanned, separated from the excitation by dichroic mirrors (F48-640, F33-554, and F38-484, AHF), filtered using appropriate emission filters (F42-652&F47-686, F47-586, and F37-510, AHF) and photons are counted using fibre-coupled APDs (APDs SPCM-AQRH-14-FC, fibres SPCM-QC9, Perkin Elmer). The multimode fibres serve as confocal pinholes that provide background rejection, thus increasing the signal-to-background ratio such that single fluorophores can still be resolved on the DNA even when high concentrations of labelled proteins are present in solution. Because the confocal pinhole size is large (~1.75 Airy disks), the expected confocal imaging resolution is set by the focal intensity distribution of the excitation beam. To block the STED beam from the detection paths, a multi-photon emission filter (F75-750, AHF) is used.

In one embodiment, the hardware control and data acquisition can be as follows. For force detection, we sample the output voltages of the PSDs at 50 kHz using a data acquisition card (NI PCI-4472B, National Instruments). Photon counting, beam steering, and digital I/O is performed using a multifunction card (NI PCIe-6323, National Instruments). All optical trapping, force detection, and confocal fluorescence and STED hardware is controlled using software, written in LabVIEW 2010 (National Instruments), and standard calibration, dumbbell-construction, mechanical characterization, and visualization procedures are largely automated. The LabVIEW software allows for automation of many of the complex experimental procedures. A hardware abstraction layer and a plug-in system enable the same software to run on a range of instruments.

In one embodiment, the focal intensity distribution imaging can be as follows. To facilitate straightforward alignment and optimization, a photomultiplier tube (PMT) is used to directly image the focal intensity distribution of the excitation and STED beams. A 50:50 beam splitter (BP145B1, Thorlabs) is placed in the beam path, and light, scattered by Au (gold) microspheres scanned through the focus using a piezo stage (NanoLP200, Mad City Labs), is detected using a PMT (MD 963 CPM DC, Perkin Elmer). Here, 80 nm Au nanoparticles (EM.GC80/4, British Biocell International) are first mounted in a 2% (w/w) agarose gel to avoid imaging near to the glass-liquid interface where reflections swamp the signal from the Au nanoparticles.

Figure 9A:
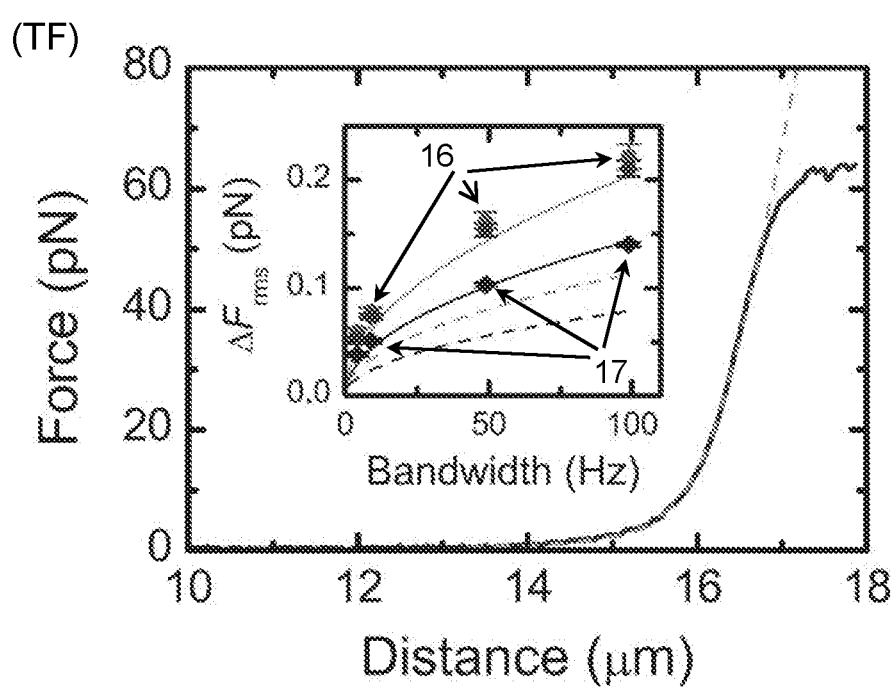
FIG. 9A-H illustrates experimental data of force spectroscopy and confocal fluorescence microscopy.
Figures 9B, 9C, 9D, 9E, 9F, 9G, 9H:
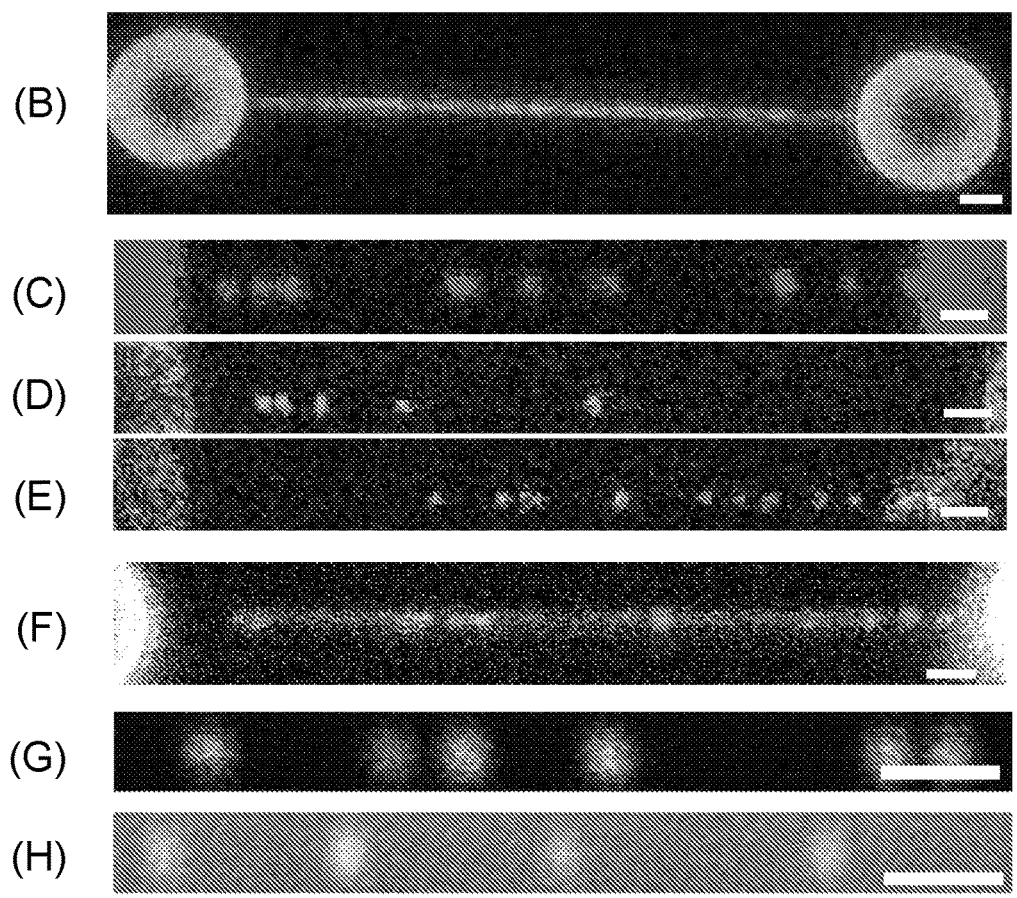

FIG. 9 illustrates experimental data of force spectroscopy and confocal fluorescence microscopy. (a) Experimental Force-distance curve of λ DNA in PBS. The dashed curve shows the worm-like-chain model calculated using a persistence length of 55 nm, a contour length of 16.5 μm, and a stretching modulus of 1350 pN. DNA overstretching occurs near 65 pN. The inset shows the force noise as function of measurement bandwidth. Points indicated by reference numeral 16 represent the force noise measured on the individual beads, points indicated by reference numeral 17 indicates the force noise in differential detection. The curves indicate the ab initio-calculated force noise limited by thermal fluctuations, where grey and black curves were calculated for single bead detection and differential detection respectively, and solid and dashed curves are calculated for 3.2 μm and 0.9 μm diameter microspheres, respectively, (b) Confocal microscopy image of Sytox Orange labelled λ DNA between two 3.2 μm microspheres (exc 543 nm). (c)-(e) Confocal microscopy images of individual EcoRV-Atto647N (exc 640 nm), Sytox Orange (exc 543 nm), and EGFP-labeled proteins (exc 467 nm), respectively, (f) Simultaneous multicolor imaging of Sytox Orange, Sytox Blue, and BsoBI-Atto647N. (g,h) Confocal microscopy images of individual BsoBI-Atto647N restriction enzymes bound specifically to optically stretched λ DNA in the absence (g), and presence (h) of a solution containing 100 nM of free Atto647N-NHS (the local concentration in the flow cell is estimated to be lower due to adsorption, approximately 40 nM). All scale bars 1 um. The typical frame rate for a 25 μm×2 μm field of view using 100 μs dwell time per 75 nm pixel is 1 Hz.

Figure 10G:
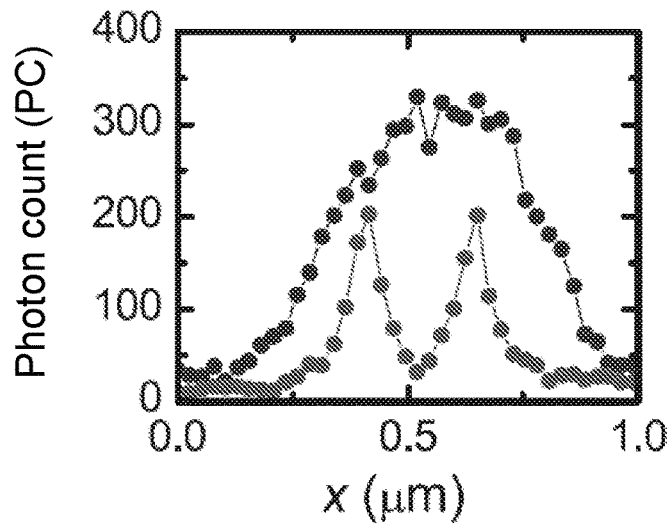
Figure 10H:
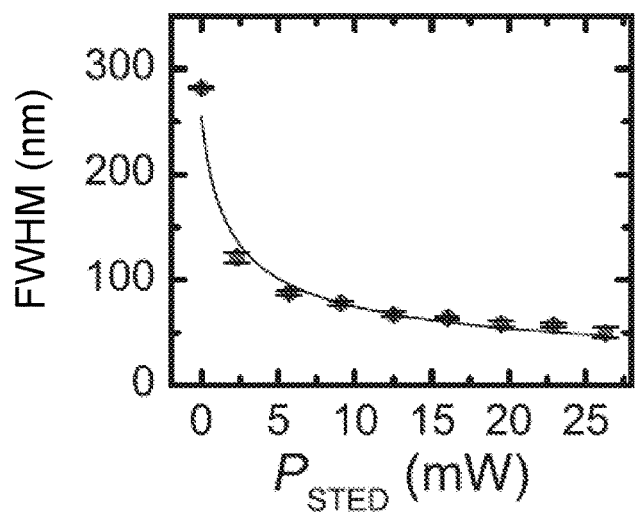
Figure 10I:
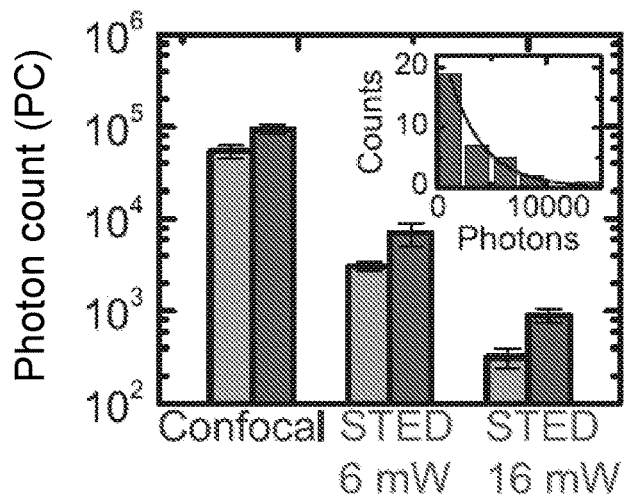

FIG. 10 illustrates characterization of STED nanoscopy of proteins on optically stretched DNA. (a,b) Focal intensity distribution of the 640 nm excitation spot imaged in XY and XZ, respectively. (c,d) Focal intensity distribution of the 745 nm STED stripe imaged in XY, and XZ. The images in (a)-(d) were acquired by detecting the back-scattered light from 80 nm Au microspheres on a PMT. (e) Confocal microscopy image of BsoBI-Atto647N on optically stretched DNA. (The elliptical shape of the intensity distributions are likely due to the linear polarization of the excitation light as well as to aberrations associated with residual tilt of the cover glass with respect to the axis of the high NA water-immersion lens.) (f) Subsequent STED microscopy image of BsoBI-Atto647N as imaged in (e). STED power 6 mW. (g) Shows projected intensity profiles of the BsoBI-Atto647N enzymes as indicated by the dashed lines in (e) and (f). (h) Resolution scaling with STED power, showing the average FWHM of Gaussian fits to intensity profiles obtained from individual BsoBI-Atto647N and EcoRV-Atto647N restriction enzymes on DNA at 5 pN tension. Error bars show standard error of the mean, (i) Shows a bar plot of the counted number of photons before photobleaching for individual fluorophores in TRIS (light grey) and ROXS (dark grey) buffers for 0 mW, 6 mW, and 16 mW STED powers. Each bar represents the exponential decay constant fitted to histograms of the number of counted photons of about 30 fluorophores (see inset).

In one embodiment, STED is employed to perform sub-diffraction imaging in optical tweezers. STED allows fast imaging on DNA at a rate that can be ultimately limited by confocal beam scanning and rate of fluorescence emission. In one embodiment, for STED, a focal intensity distribution is used that features a one-dimensional central line of nearly zero intensity (rather than a doughnut-shaped distribution). FIG. 10a-d show the focal intensity distributions of the 640 nm excitation and 745 nm STED beams. By orienting the zero-line perpendicular to the stretched DNA, the spatial resolution is enhanced along the length of the DNA only. Advantageously, this 1D-STED scheme can render 1D-line scanning less sensitive to lateral DNA fluctuations, misalignment, or drift between the optical trapping and fluorescence imaging systems than a doughnut.

FIGS. 10e and f show confocal and STED images of BsoBI-Atto647N restriction enzymes specifically bound to optically stretched DNA. A clear resolution enhancement along the DNA can be observed in the STED image, which is further illustrated in the intensity profiles of FIG. 10g. At relatively low STED power, PSTED=6 mW, a threefold enhancement of spatial resolution over confocal imaging is obtained. The scaling of resolution with STED power was further characterized by imaging restriction enzymes on optically stretched DNA. FIG. 10h shows the enhancement of resolution with increasing PSTED—At PSTED=26 mW, a resolution of 50+/−5 nm FWHM was obtained, corresponding to a 6-fold resolution enhancement over confocal imaging under the same conditions (given by the water immersion lens and the aqueous medium). Most notably, this gain in resolution allows imaging DNA-protein complexes in optical tweezers at a resolution comparable to the persistence length of DNA.

Figure 11:
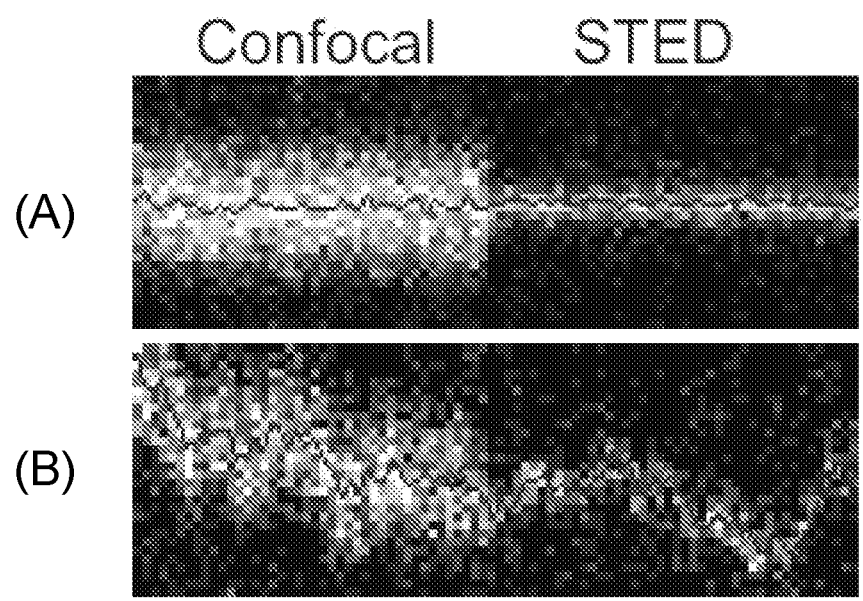
FIG. 11A-D illustrates characterization of localization precision.
Figure 11C:
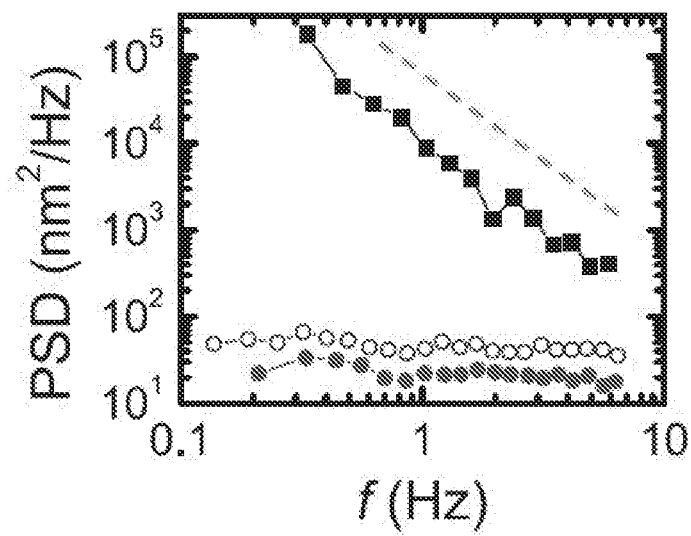
Figure 11D:
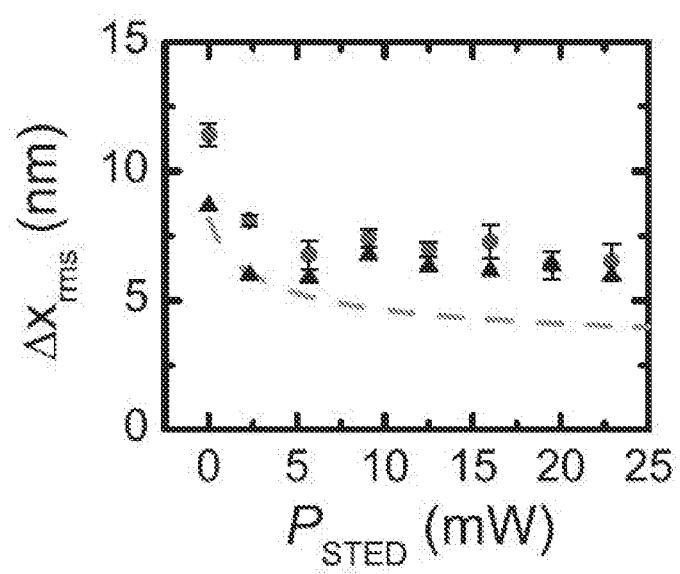
Figure 12A:
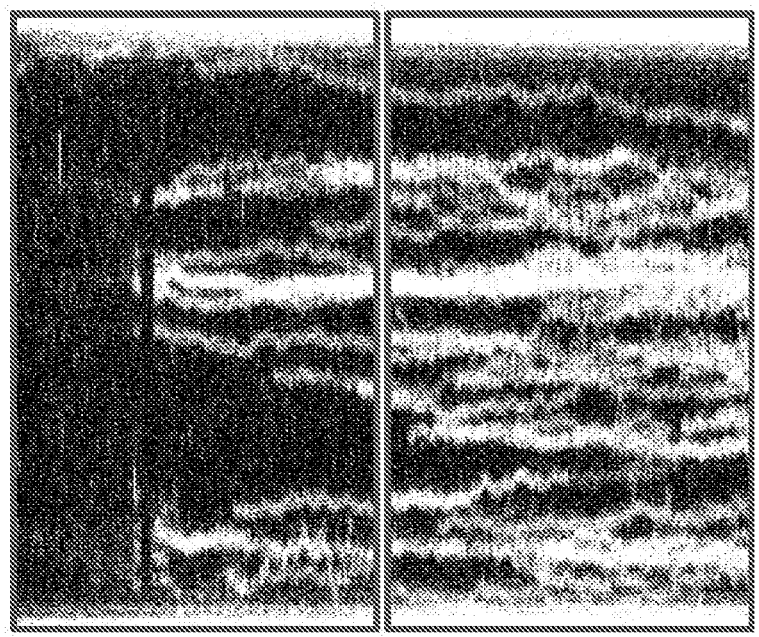
FIG. 12A-F illustrates TFAM binding and diffusion dynamics on optically stretched DNA.
Figure 12B:
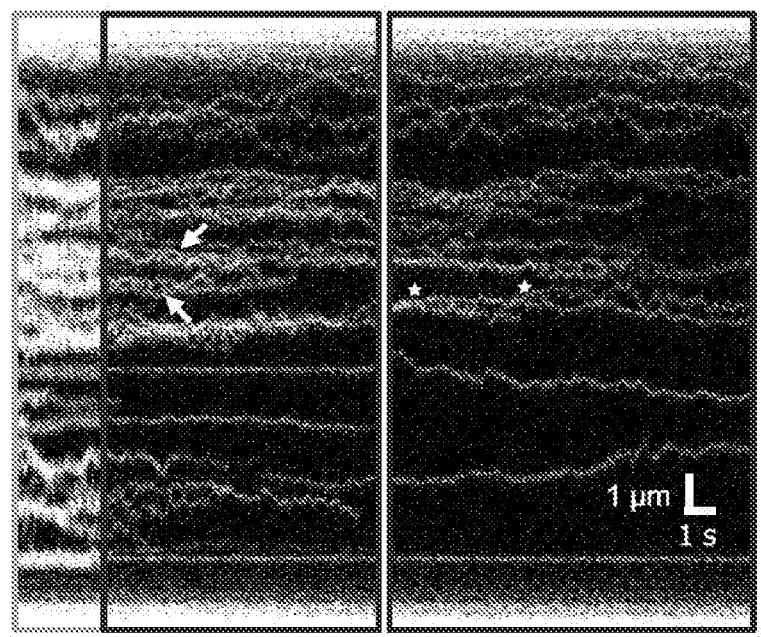
Figure 12C:
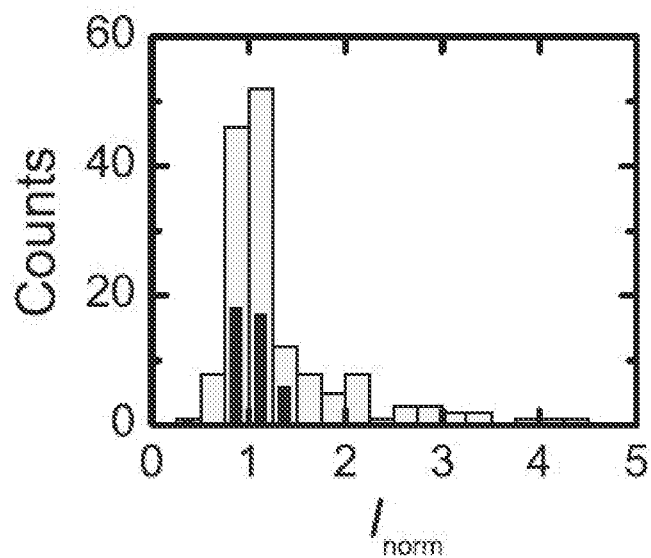
Figure 12D:
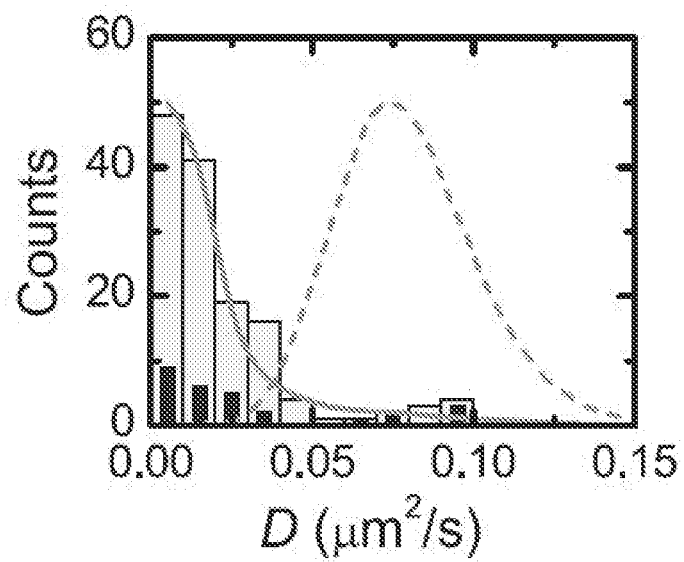
Figure 12E:
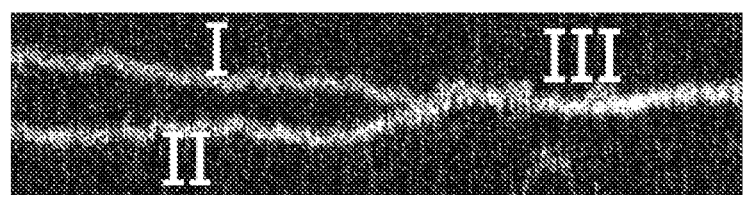
Figure 12F:
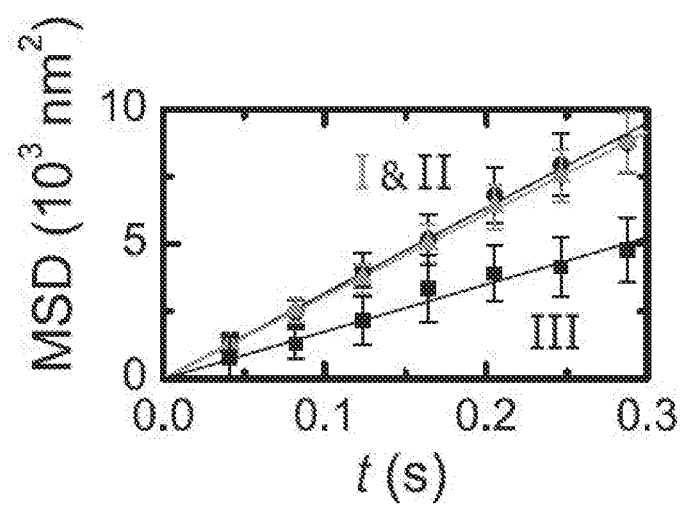

FIG. 11 illustrates characterization of localization precision. (a) Kymograph of EcoRV-Atto647N immobilized on optically stretched DNA (kymograph dimensions are 17.4 s by 750 nm). (b) Kymograph of TFAM-Atto647N diffusing on optically stretched DNA (kymograph dimensions are 9.6 s by 750 nm). Transcription factor A, mitochondrial (TFAM) is a protein that in humans is encoded by the TFAM gene. The kymographs of (a) and (b) were imaged partially by confocal microscopy, and partially by STED nanoscopy (PSTED=6 mW). The red lines track the centres of the photon distributions and were obtained by fitting 1D Gaussians to each pixel column. (c) Shows power-spectral density (PSD) for tracked positions of proteins on DNA. The black squares show the PSD for a single TFAM-Atto647N diffusing on DNA. The dashed line indicates $1/f^2$ behaviour. The circles indicate averaged PSDs for BsoBI-Atto647N immobilized on DNA for confocal imaging (blue, open) and STED imaging (red, filled), (d) Shows the localization precision Δxrms as function of STED power. Red circles show the localization precision as obtained from tracking immobilized proteins on DNA, black triangles show the ideal localization precision calculated for the same dataset, and the dashed line indicates the optimal ideal localization precision that assumes no loss in peak brightness of the fluorophores with increasing STED power. In all experiments, the DNA tension was ~5 pN.

FIG. 12 illustrates TFAM binding and diffusion dynamics on optically stretched DNA. (a) Confocal kymographs. As the DNA (at ~5 pN tension) is moved into a channel with 50 nM human TFAM-Atto647N (estimated concentration is lower due to adsorption, approximately 5 nM), TFAM molecules bind to the DNA and undergo one-dimensional diffusion along the DNA. (b) Kymographs of TFAM-Atto647N dynamics on optically stretched DNA imaged in ROXS buffer. Initially the STED beam is off (blue rectangle). After ~5 s the STED beam is switched on at 6 mW as indicated by the red rectangles. Imaging in (a) and (b) was performed at 10 µs per 25 nm pixel, line rate 90 Hz, 5-line averages are displayed. (c,d) Histograms of the normalized intensity, lnorm, and diffusion coefficient, D, of TFAM-Atto647N on DNA (N=143) obtained both by STED and confocal imaging. The blue bars indicate TFAM immediately after binding DNA (N=42), while red bars indicate the full dataset (N=143), including already bound TFAM and TFAM filaments. The intensity data of (c) was normalized to the intensity of a single fluorophore. D was calculated by fitting the mean-squared-displacement (MSD) determined from individual traces (consisting of about 150+/−75 linescans, with a minimum of 50 lines) to MSD=2Dt+offset. The curves in (d) indicate normalized distributions of D calculated for simulated diffusion data with Dref=0.08 µm²/s (dashed) and with a range of diffusion constants D=Drefin where n=1, 2, 3, . . . , 12 (solid), (e) Kymograph of a TFAM-Atto647N oligomerization event (line rate 90 Hz, 5-line average displayed), (f) MSD analysis of trajectories I-III as displayed in (e).

Figure 13A:
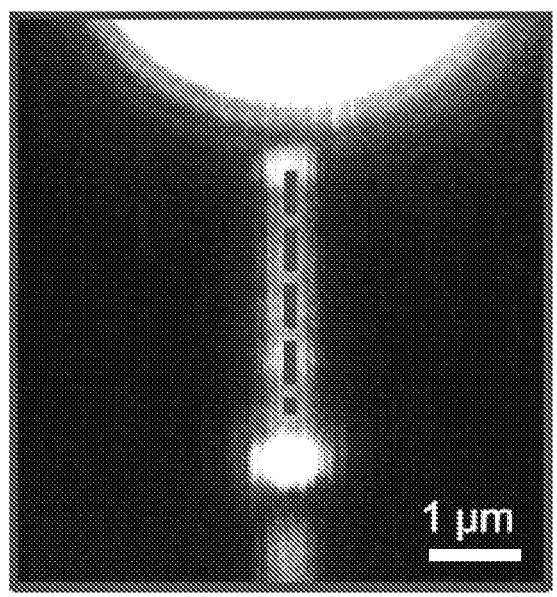
FIG. 13A-C illustrates STED nanoscopy of DNA that is densely coated with TFAM.
Figure 13B:
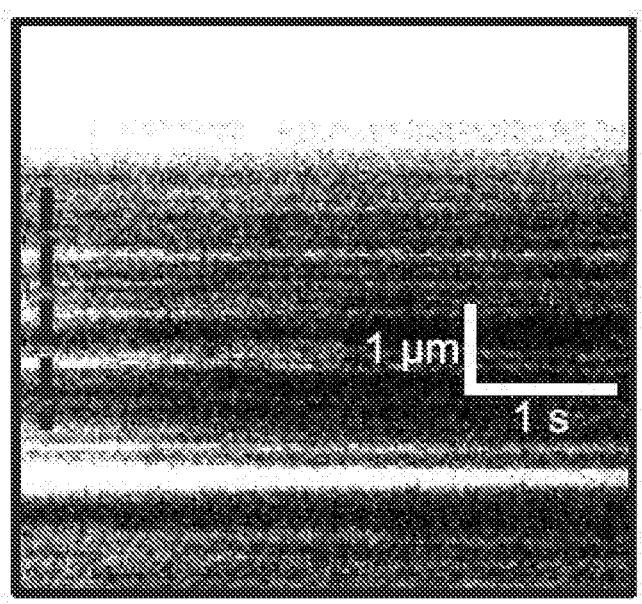
Figure 13C:
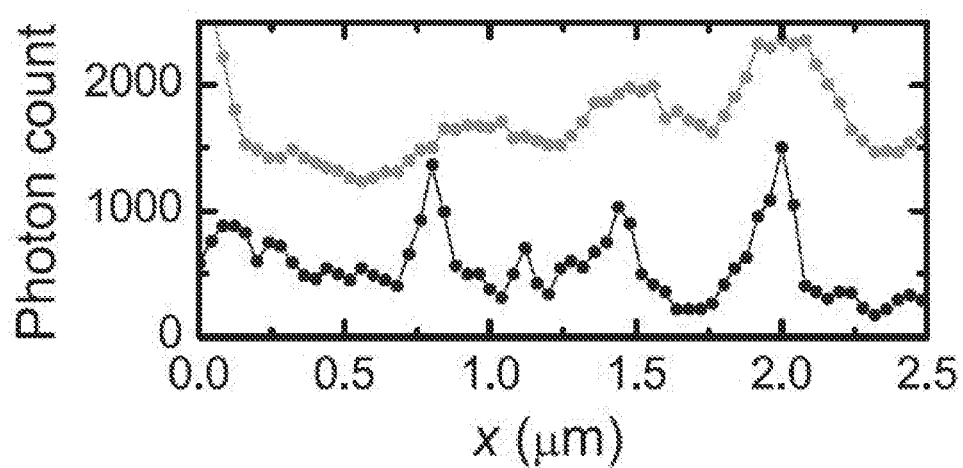

FIG. 13 illustrates STED nanoscopy of DNA that is densely coated with TFAM. (a) Confocal microscopy image of TFAM-Atto647N filaments at high density on DNA. (b) STED kymograph of the section of the DNA imaged in (b). STED power 16 mW. (c) Cumulative intensity profile as indicated in (a) (top line) and (b) (bottom line), comparing confocal and STED profiles.

It will be appreciated that, while example embodiments were shown for methods and systems for imaging a molecular strand, also alternative ways may be envisaged by those skilled in the art having the benefit of the present disclosure for achieving similar functions and results. E.g. optical and/or electrical components may be combined or split up into one or more alternative components, e.g. curved mirrors instead or in addition to lenses, different detectors or light sources, et cetera. The various elements of the embodiments as discussed and shown offer certain advantages, such as high precision and control geared to the imaging of one-dimensional molecule sized strands. Of course, it is to be appreciated that any one of the above embodiments or processes may be combined with one or more other embodiments or processes to provide even further improvements in finding and matching designs and advantages. It is appreciated that this disclosure offers particular advantages to the study of molecular biology and in general can be applied for any application wherein a molecular strand is imaged. While the present disclosure provides specific advantages by using STED, in particular 1D-STED, also other super-resolution techniques may be envisaged to be combined with the present systems and methods such as PALM/STORM. While the use of optical traps provide unique advantages in control over the capture and aligning of the strand, also alternatives may be used for trapping the strand. For example, also other trapping and extending mechanisms can be employed such as magnetic tweezers or flow stretching. Also combinations are possible, e.g. one end of the strand can be held by an optical or magnetic trap while the strand is stretched by flow stretching. The strand may also be trapped by attachment to a larger structure such as a glass slide and flow stretched or an attachment point embedded in a supported lipid bilayer.

While the present systems and methods have thus been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function are considered to implicitly disclose the method or function as such and/or in combination with other disclosed embodiments of methods or systems. Furthermore, embodiments of methods are considered to implicitly disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. Method for imaging a molecular strand, the method comprising providing a sample volume comprising the strand with trapping beads attached on opposite ends of the strand;

providing an excitation beam having an excitation focus in the sample volume wherein an excitation of a fluorophore on the strand by the excitation focus results in a fluorescence response when the excitation focus coincides with the fluorophore;

scanning the excitation focus in the sample volume along a one dimensional scanning line;

providing optical traps, trapping the trapping beads at the ends of the strand in the sample volume and extending the strand between the optical traps to form a one-dimensional trapping line parallel to the scanning line;

aligning the trapping line to coincide with the scanning line to have the scanning excitation focus coincide with the strand; and recording the fluorescence response as a function of a plurality of distinct scanning positions of the excitation focus along the scanning line.

2. Method according to claim 1, comprising providing a depletion beam having a depletion focus with a depletion profile coinciding with an excitation profile of the excitation focus and causing stimulated emission depletion of the excitation of the fluorophore according to the depletion profile, wherein the depletion profile has a minimum intensity at a centre of the excitation focus for reducing the area where spontaneous fluorescent emission occurs wherein the depletion profile comprises a region of minimum intensity coinciding with the trapping line.

3. Method according to claim 1, comprising providing a depletion beam having a depletion focus with a depletion profile coinciding with an excitation profile of the excitation focus and causing stimulated emission depletion of the excitation of the fluorophore according to the depletion profile, wherein the depletion profile has a minimum intensity at a centre of the excitation focus for reducing a profile size of excited fluorophores by the stimulated emission depletion wherein the depletion profile comprises a plane of minimum intensity extending perpendicular to the trapping line.

4. Method according to claim 1, wherein one or more optically trapped beads are attached to the strand for trapping the strand, wherein the beads exert a tensile force on the strand to suppress thermal fluctuations of the strand to a value below the diffraction limit.

5. Method according to claim 1, wherein optically trapped beads are attached to the strand, wherein the beads have a diameter larger than a waist of a trapping beam trapping the beads.

6. Method according to claim 1, wherein the fluorescence response is recorded at an image plane which image plane is a conjugate focal plane of an object plane in the sample volume, wherein the object plane extends in the first direction and wherein the excitation focus and trapping line are aligned to coincide with the object plane wherein a spatial pinhole is provided in the image plane, wherein the spatial pinhole is aligned to coincide with a conjugate focal point of the excitation focus for passing the fluorescence response through the spatial pinhole to a fluorescence detector.

7. Method according to claim 1, wherein the excitation focus is repeatedly scanned back and forth along the scanning line wherein the fluorescence response is distinguished between the plurality of distinct scanning positions along the scanning line and/or integrated over multiple scans and/or recorded as a function of time.

8. Method according to claim 1, wherein the sample volume is comprised in a sample cell comprising a sample window transparent to incoming excitation and/or depletion beams, wherein the sample cell comprises rotational actuators for tilting and/or rotating the sample cell, wherein the method further comprises aligning the sample window to be perpendicular to the incoming beams for optimizing a profile of the excitation focus and/or depletion focus.

9. Method according to claim 1, further comprising measuring interaction of a fluorescent reagent with a molecular strand by;

providing a microfluidic flow cell FC wherein separate input channels of the flow cell provide a plurality of separate laminar flows in a sample volume of the flow cell, wherein a first laminar flow comprises a plurality of beads arranged for attaching to opposite ends of the molecular strand;

a second laminar flow comprises a plurality of the molecular strands; and a third laminar flow comprises the reagent;

providing an optical trap in the first laminar flow and trapping a bead with the optical trap;

positioning the optical trap to the second laminar flow and attaching the bead to a strand;

positioning the optical trap to the third laminar flow; and using a method according to any of the previous claims for recording the fluorescence response of the reagent.

10. Method according to claim 9, wherein the molecular strand is a DNA or RNA strand and the fluorescent reagent comprises a reagent that associates with the molecular strand such as protein molecules.

11. System for imaging a molecular strand, the system comprising a sample cell arranged for providing a sample volume comprising the strand;

an excitation light source arranged for providing an excitation beam having an excitation focus in the sample volume wherein an excitation of a fluorophore on the strand by the excitation focus results in a fluorescence response when the excitation focus coincides with the fluorophore;

a beam scanner arranged for scanning the excitation focus in the sample volume along a one dimensional scanning line;

a trap arranged for trapping an end of the strand in the sample volume and extending the strand along a one-dimensional trapping line parallel to the scanning line, wherein the trap comprises a trapping light source and trapping beam optics arranged for providing optical traps trapping beads attached on opposite ends of the strand, wherein the optical traps are arrange to form the trapping line between the beads;

a beam aligner arranged for aligning the trapping line to coincide with the scanning line to have the scanning excitation focus coincide with the strand; and a fluorescence detector arranged for recording the fluorescence response as a function of a plurality of distinct scanning positions of the excitation focus along the scanning line; and a processor programmed to provide a scanning mode wherein the processor controls the trap to extend the strand along a one-dimensional trapping line in the first direction;

the processor controls the beam aligner to have the trapping line coincide with the scanning line;

the processor controls the beam scanner to scan the excitation focus along the scanning line;

the processor receives the recorded fluorescence response from the fluorescence detector; and the processor stores the fluorescence response at one or more positions of the excitation focus along the scanning line.

12. System according to claim 11, further comprising
a depletion light source and depletion beam optics arranged for providing a depletion beam having a depletion focus with a depletion profile coinciding with an excitation profile of the excitation focus and causing stimulated emission depletion of the excitation of the fluorophore according to the depletion profile, wherein the depletion profile has a minimum intensity at a centre of the excitation focus for reducing a profile size of excited fluorophores by the stimulated emission depletion;
a depletion focus shaper arranged for shaping the depletion profile wherein the depletion profile comprises a plane of minimum intensity extending perpendicular to the trapping line.

13. System according to claim 11, wherein
the sample cell comprises a microfluidic flow cell FC wherein separate input channels of the flow cell provide a plurality of separate laminar flows in a sample volume of the flow cell;
the trap comprises optical traps trapping beads attached on opposite ends of the strand, wherein the optical traps are arranged to form the trapping line between the beads;
wherein the optical traps are moveable between the laminar flows.

* * * * *